United States Patent
Koyama et al.

(10) Patent No.: US 8,637,623 B2
(45) Date of Patent: Jan. 28, 2014

(54) MONOMER HAVING ELECTRON-WITHDRAWING SUBSTITUENT AND LACTONE SKELETON, POLYMERIC COMPOUND, AND PHOTORESIST COMPOSITION

(75) Inventors: Hiroshi Koyama, Himeji (JP); Kyuhei Kitao, Himeji (JP); Akira Eguchi, Himeji (JP)

(73) Assignee: Daicel Chemical Industries, Ltd., Osaka (JP)

( * ) Notice: Subject to any disclaimer, the term of this patent is extended or adjusted under 35 U.S.C. 154(b) by 529 days.

(21) Appl. No.: 12/863,924

(22) PCT Filed: Feb. 3, 2009

(86) PCT No.: PCT/JP2009/000402
§ 371 (c)(1), (2), (4) Date: Jul. 21, 2010

(87) PCT Pub. No.: WO2009/107327
PCT Pub. Date: Sep. 3, 2009

(65) Prior Publication Data
US 2010/0297555 A1 Nov. 25, 2010

(30) Foreign Application Priority Data
Feb. 25, 2008 (JP) ................................. 2008-043501

(51) Int. Cl.
| | | |
|---|---|---|
| C08F 20/10 | (2006.01) | |
| C08F 20/22 | (2006.01) | |
| C08F 20/26 | (2006.01) | |
| C08F 20/34 | (2006.01) | |
| C07D 317/06 | (2006.01) | |
| C07C 69/01 | (2006.01) | |
| C07C 69/013 | (2006.01) | |
| G03F 7/004 | (2006.01) | |
| G03F 7/26 | (2006.01) | |

(52) U.S. Cl.
USPC ........ 526/318; 430/270.1; 430/322; 549/295; 549/297; 549/298; 560/205; 560/220

(58) Field of Classification Search
USPC .......... 430/270.1, 326, 322; 526/318, 318.44; 549/1, 12, 13, 211, 221, 237, 263, 273, 549/275, 293, 296, 299, 295, 297, 298; 560/205, 220
See application file for complete search history.

(56) References Cited

U.S. PATENT DOCUMENTS

| | | | | |
|---|---|---|---|---|
| 2004/0248031 A1* | 12/2004 | Ansai et al. | ................ | 430/270.1 |
| 2005/0260525 A1* | 11/2005 | Takemoto et al. | ......... | 430/270.1 |
| 2007/0134588 A1* | 6/2007 | Kanda et al. | ................ | 430/270.1 |
| 2007/0218401 A1* | 9/2007 | Ando et al. | ................. | 430/270.1 |
| 2008/0026331 A1 | 1/2008 | Hasegawa et al. | | |
| 2008/0268370 A1* | 10/2008 | Tanaka et al. | ................ | 430/270.1 |
| 2008/0319160 A1 | 12/2008 | Inoue et al. | | |
| 2009/0246695 A1 | 10/2009 | Yamaguchi et al. | | |
| 2009/0325102 A1* | 12/2009 | Shibuya et al. | ............ | 430/270.1 |

FOREIGN PATENT DOCUMENTS

| | | |
|---|---|---|
| JP | 10-274852 A | 10/1998 |
| JP | 2000-26446 A | 1/2000 |
| JP | 2005-48128 A | 2/2005 |
| JP | 2007-249192 A | 9/2007 |
| JP | 2008-31298 A | 2/2008 |
| JP | 2008-129388 A | 6/2008 |
| JP | 2008-231059 A | 10/2008 |
| WO | WO 2007/037213 A1 | 4/2007 |

OTHER PUBLICATIONS

International Search Report, dated Apr. 21, 2009, issued in PCT/JP2009/000402.

* cited by examiner

*Primary Examiner* — Anca Eoff
(74) *Attorney, Agent, or Firm* — Birch, Stewart, Kolasch & Birch, LLP

(57) ABSTRACT

Disclosed is a monomer having an electron-withdrawing substituent and a lactone skeleton, represented by Formula (1), wherein $R^a$ represents, e.g., hydrogen or an alkyl group having 1 to 6 carbons; $R^1$ represents, e.g., a halogen or an alkyl or haloalkyl group having 1 to 6 carbons; "A" represents an alkylene group having 1 to 6 carbons, oxygen, sulfur, or is nonbonding; "m" denotes an integer of 0 to 8; Xs each represent an electron-withdrawing substituent; "n" denotes an integer of 1 to 9; and Y represents a bivalent organic group having 1 to 6 carbons. The monomer is useful as a monomer component typically for a highly functional polymer, because, when the monomer is applied to a resist resin, the resin is stable and resistant to chemicals, is highly soluble in organic solvents, and has improved hydrolyzability and/or solubility in water after hydrolysis.

[Chemical Formula 1]

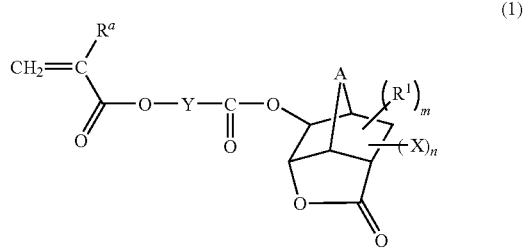

(1)

12 Claims, No Drawings

MONOMER HAVING ELECTRON-WITHDRAWING SUBSTITUENT AND LACTONE SKELETON, POLYMERIC COMPOUND, AND PHOTORESIST COMPOSITION

TECHNICAL FIELD

The present invention relates to monomers, polymeric compounds, and photoresist compositions for use in photoresists adopted typically to fine patterning of semiconductor devices (semiconductors); and to processes for manufacturing semiconductor devices using the photoresist compositions.

BACKGROUND ART

Recent dramatic innovation on lithography techniques for patterning in the manufacture of semiconductor devices has made lithographic line widths finer and finer. In lithographic exposure, i-ray and g-ray were initially used to give patterns with broad line widths, and the fabricated semiconductor devices thereby had low capacities. However, recent technological development has allowed the use of KrF excimer laser to give patterns with dramatically finer line widths. Thereafter the technological development has continued so as to adopt ArF excimer laser having a further shorter wavelength to lithographic exposure, and this has been achieved in very recent years. Common resins, i.e., novolak or styrenic resins, have been used in exposure to KrF excimer laser. However, in exposure to ArF excimer laser, the novolak or styrenic resins have been replaced with resins containing no aromatic moieties, i.e., with alicyclic resins, because the ArF excimer laser has a further shorter wavelength of 193 nm, and resins containing aromatic moieties, such as novolak or styrenic resins, absorb the light of this wavelength. Predominant resins used in exposure to ArF excimer laser are acrylic resins. In a mechanism applied in these acrylic resins, acrylic acid has been protected by a protecting group, and upon exposure (light irradiation), an acid is generated and acts to allow the protecting group to leave, i.e., to deprotect the protected acrylic acid into carboxylic acid, and this makes the resins to be soluble in an alkali. Most of currently used protecting groups are alicyclic groups having no polar group. However, these groups, when used alone, have insufficient adhesion to a substrate and lack affinity typically for an alkaline developer, and many acrylic monomers having a polar-group-containing alicyclic skeleton as an ester group have been proposed. Among them, monomers having an alicyclic skeleton containing a lactone ring as a polar group have been highly evaluated on their functions and have been used in large numbers. A part of such monomers can be found in Patent Document 1. Independently, the use of a lactone ring as a monocyclic ester group acting as the protecting group has been proposed typically in Patent Document 2. However, such monocyclic ester group lacks the most important function necessary for resists, i.e., etching resistance, and seems to be not so widely used. Strong demands are now made on monomers having satisfactory etching resistance, because there is developed a technique called immersion lithography in which a space between the substrate and an exposure system is filled with a liquid having a high density; and this technique allows resist patterns to be finer and finer, and along with this, the resist films tend to have smaller and smaller thicknesses. In addition, strong demands are also made on resins for use in resists to have improved solubility in organic solvents, because resins containing large quantities of alicyclic acrylic esters having lactone rings are insufficient in solubility in organic solvents such as resist solvents.

Patent Document 1: Japanese Unexamined Patent Application Publication (JP-A) No. 2000-026446
Patent Document 2: Japanese Unexamined Patent Application Publication (JP-A) No. H10 (1998)-274852

DISCLOSURE OF INVENTION

Problems to be Solved by the Invention

Accordingly, an object of the present invention is to provide a novel monomer having a lactone skeleton, a resin derived from the monomer, a photoresist composition using the resin, and a process for manufacturing a semiconductor device using the photoresist composition, in which the monomer is useful typically as a monomer component typically for a highly functional polymer, because, when the monomer is applied typically to a resist resin, the resin can remain being satisfactorily stable and resistant typically to chemicals, is satisfactorily soluble in organic solvents, and can be more satisfactorily hydrolyzable and/or the hydrolyzed product thereof is more satisfactorily soluble in water. Another object of the present invention is to provide a resin which shows high etching resistance when used as a photoresist resin to thereby provide a photoresist resin and a composition containing the photoresist resin for use particularly in immersion lithography.

Means for Solving the Problems

After intensive investigations on monomers having lactone skeletons for use in photoresist resins, the present inventors have found a monomer which gives a resin that is satisfactorily soluble in solvents and shows high resist performance. The present invention has been made based on these findings.

Specifically, the present invention provides, in an embodiment, a monomer having an electron-withdrawing substituent and a lactone skeleton, which is represented by following Formula (1):

[Chemical Formula 1]

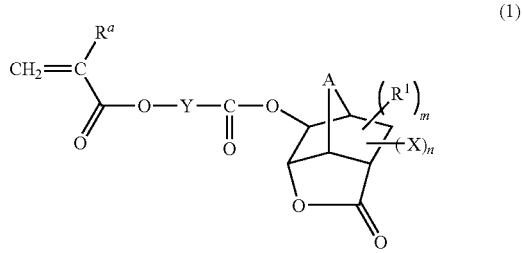

wherein $R^a$ represents a hydrogen atom, a halogen atom, or a substituted or unsubstituted alkyl group having 1 to 6 carbon atoms; $R^1$ is a substituent bound to the ring and represents a halogen atom, an alkyl or haloalkyl group having 1 to 6 carbon atoms, a hydroxyalkyl or hydroxyhaloalkyl group having 1 to 6 carbon atoms whose hydroxyl moiety may be protected by a protecting group, a carboxyl group which may form a salt, or a substituted oxycarbonyl group; "A" represents an alkylene group having 1 to 6 carbon atoms, an oxygen atom, a sulfur atom, or nonbonding; "m" is the number of $R^1$s and denotes an integer of 0 to 8; Xs each represent an electron-withdrawing substituent; "n" is the number of Xs bound to the ring and denotes an integer of 1 to 9; and Y represents a bivalent organic group having 1 to 6 carbon atoms, wherein the $CH_2=C(R^a)COO—Y—COO—$ group may have either endo or exo configuration.

The present invention provides, in another embodiment, a polymeric compound including at least a monomeric unit represented by following Formula (I):

[Chemical Formula 2]

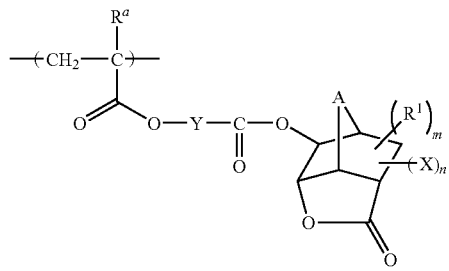

(I)

wherein $R^a$ represents a hydrogen atom, a halogen atom, or a substituted or unsubstituted alkyl group having 1 to 6 carbon atoms; $R^1$s are substituents bound to the ring and each represent a halogen atom, an alkyl or haloalkyl group having 1 to 6 carbon atoms, a hydroxyalkyl or hydroxyhaloalkyl group having 1 to 6 carbon atoms whose hydroxyl moiety may be protected by a protecting group, a carboxyl group which may form a salt, or a substituted oxycarbonyl group; "A" represents an alkylene group having 1 to 6 carbon atoms, an oxygen atom, a sulfur atom, or nonbonding; "m" is the number of $R^1$s and denotes an integer of 0 to 8; Xs each represent an electron-withdrawing substituent; "n" is the number of Xs bound to the ring and denotes an integer of 1 to 9; and Y represents a bivalent organic group having 1 to 6 carbon atoms, wherein the —COO—Y—OOO— group bound to the polymer chain may have either endo or exo configuration.

The polymeric compound may further include at least a monomeric unit part of which will leave with an acid to allow the polymeric compound to be soluble in an alkali, in addition to the monomeric unit represented by Formula (I).

The monomeric unit part of which will leave with an acid to allow the polymeric compound to be soluble in an alkali may for example be a monomeric unit selected from monomeric units represented by following Formulae (IIa), (IIb), (IIc), and (IId):

[Chemical Formula 3]

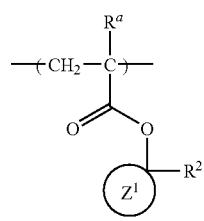

(IIa)

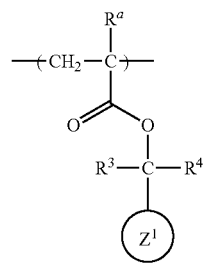

(IIb)

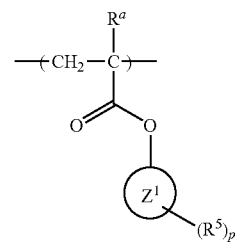

(IIc)

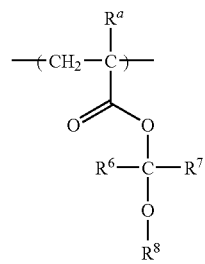

(IId)

wherein Ring $Z^1$ represents a substituted or unsubstituted alicyclic hydrocarbon ring having 5 to 20 carbon atoms; $R^a$ represents a hydrogen atom, a halogen atom, or a substituted or unsubstituted alkyl group having 1 to 6 carbon atoms; $R^2$, $R^3$, and $R^4$ are the same as or different from one another and each represent a substituted or unsubstituted alkyl group having 1 to 6 carbon atoms; $R^5$s are substituents bound to Ring $Z^1$, are the same as or different from each other, and each represent oxo group, an alkyl group, a protected or unprotected hydroxyl group, a protected or unprotected hydroxyalkyl group, or a protected or unprotected carboxyl group, wherein at least one of $pR^5$s represents a —$COOR^c$ group, wherein $R^c$ represents a substituted or unsubstituted tertiary hydrocarbon group, a tetrahydrofuranyl group, a tetrahydropyranyl group, or an oxepanyl group; "p" denotes an integer of 1 to 3; $R^6$ and $R^7$ are the same as or different from each other and each represent a hydrogen atom or a substituted or unsubstituted alkyl group having 1 to 6 carbon atoms; and $R^8$ represents a hydrogen atom or an organic group, wherein at least two of $R^6$, $R^7$, and $R^8$ may be bound to each other to form a ring with an adjacent atom.

The polymeric compound may further include at least a monomeric unit containing an alicyclic skeleton having at least one substituent, in addition to the monomeric unit represented by Formula (I).

The monomeric unit containing an alicyclic skeleton having at least one substituent may for example be a monomeric unit selected from monomeric units represented by following Formula (III):

[Chemical Formula 4]

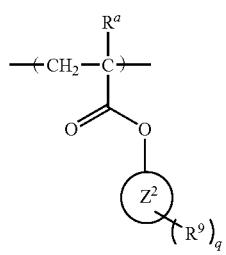

(III)

wherein Ring $Z^2$ represents an alicyclic hydrocarbon ring having 6 to 20 carbon atoms; $R^a$ represents a hydrogen atom, a halogen atom, or a substituted or unsubstituted alkyl group having 1 to 6 carbon atoms; $R^9$s are substituents bound to Ring $Z^2$, are the same as or different from each other, and each represent an oxo group, an alkyl group, a haloalkyl group, a halogen atom, a protected or unprotected hydroxyl group, a protected or unprotected hydroxyalkyl group, a protected or unprotected mercapto group, a protected or unprotected carboxyl group, a protected or unprotected amino group, or a protected or unprotected sulfonic group; and "q" is the number of $R^9$s and denotes an integer of 1 to 5.

The polymeric compound preferably contains at least the monomeric unit represented by Formula (I); the monomeric unit part of which will leave with an acid to allow the polymeric compound to be soluble in an alkali; and a monomeric unit containing an alicyclic skeleton having at least one substituent selected from hydroxyl group and hydroxymethyl group.

The polymeric compound may further include at least another monomeric unit having a lactone skeleton than the monomeric unit represented by Formula (I), in addition to the monomeric unit represented by Formula (I).

The present invention provides, in still another embodiment, a photoresist composition containing at least the polymeric compound and a light-activatable acid generator.

In yet another embodiment, the present invention provides a process for manufacturing a semiconductor device. This process includes the step of forming a pattern using the photoresist composition.

The present invention provides, in another embodiment, a halogen-containing lactone compound represented by following Formula (6):

[Chemical Formula 5]

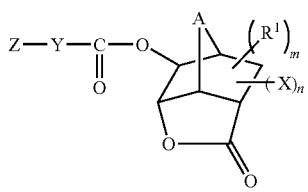

(6)

wherein $R^1$s are substituents bound to the ring and each represent a halogen atom, an alkyl or haloalkyl group having 1 to 6 carbon atoms, a hydroxyalkyl or hydroxyhaloalkyl group having 1 to 6 carbon atoms whose hydroxyl moiety may be protected by a protecting group, a carboxyl group which may form a salt, or a substituted oxycarbonyl group; "A" represents an alkylene group having 1 to 6 carbon atoms, an oxygen atom, a sulfur atom, or nonbonding; "m" is the number of $R^1$s and denotes an integer of 0 to 8; Xs each represent an electron-withdrawing substituent; "n" is the number of Xs bound to the ring and denotes an integer of 1 to 9; Z represents a chlorine atom, a bromine atom, or an iodine atom; and Y represents a bivalent organic group having 1 to 6 carbon atoms, wherein the Z—Y—COO— group may have either endo or exo configuration.

The present invention further provides, in still another embodiment, a process for producing a monomer having an electron-withdrawing substituent and a lactone skeleton. This process includes the step of reacting a halogen-containing lactone compound represented by following Formula (6):

[Chemical Formula 6]

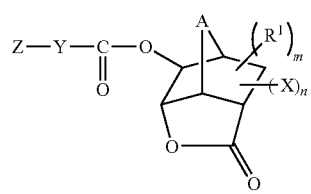

(6)

wherein $R^1$s are substituents bound to the ring and each represent a halogen atom, an alkyl or haloalkyl group having 1 to 6 carbon atoms, a hydroxyalkyl or hydroxyhaloalkyl group having 1 to 6 carbon atoms whose hydroxyl moiety may be protected by a protecting group, a carboxyl group which may form a salt, or a substituted oxycarbonyl group; "A" represents an alkylene group having 1 to 6 carbon atoms, an oxygen atom, a sulfur atom, or nonbonding; "m" is the number of $R^1$s and denotes an integer of 0 to 8; Xs each represent an electron-withdrawing substituent; "n" is the number of Xs bound to the ring and denotes an integer of 1 to 9; Z represents a chlorine atom, a bromine atom, or an iodine atom; and Y represents a bivalent organic group having 1 to 6 carbon atoms, wherein the Z—Y—COO— group may have either endo or exo configuration with an unsaturated carboxylic acid, or an alkali metal salt or alkaline earth metal salt thereof, represented by following Formula (7):

[Chemical Formula 7]

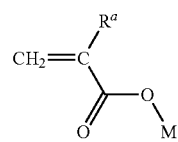

(7)

wherein $R^a$ represents a hydrogen atom, a halogen atom, or a substituted or unsubstituted alkyl group having 1 to 6 carbon atoms; and M represents a hydrogen atom, an alkali metal, or an alkaline earth metal, to give the monomer having an electron-withdrawing substituent and a lactone skeleton, represented by following Formula (1):

[Chemical Formula 8]

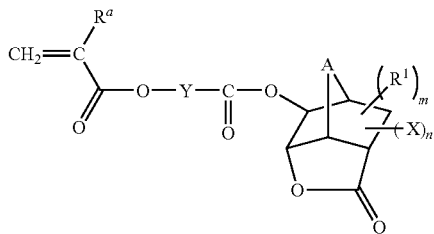

(1)

wherein $R^a$ represents a hydrogen atom, a halogen atom, or a substituted or unsubstituted alkyl group having 1 to 6 carbon atoms; $R^1$s are substituents bound to the ring and each represent a halogen atom, an alkyl or haloalkyl group having 1 to 6 carbon atoms, a hydroxyalkyl or hydroxyhaloalkyl group having 1 to 6 carbon atoms whose hydroxyl moiety may be protected by a protecting group, a carboxyl group which may form a salt, or a substituted oxycarbonyl group; "A" represents an alkylene group having 1 to 6 carbon atoms, an oxygen atom, a sulfur atom, or nonbonding; "m" is the number of $R^1$s and denotes an integer of 0 to 8; Xs each represent an electron-withdrawing substituent; "n" is the number of Xs bound to the ring and denotes an integer of 1 to 9; and Y represents a bivalent organic group having 1 to 6 carbon atoms, wherein the $CH_2=C(R^a)COO-Y-COO-$ group may have either endo or exo configuration.

The locants (position numbers) in 6-oxabicyclo[3.2.1$^{1,5}$] octane ring and those in 3-oxatricyclo[4.2.1.0$^{4,8}$]nonane ring are shown below in the left and right formulae, respectively.

[Chemical Formula 9]

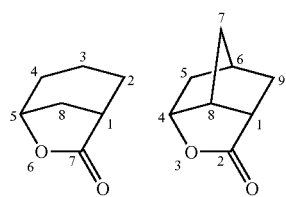

Advantages

The present invention provides a novel monomer having a polycyclic ester group containing a lactone skeleton, a resin derived from the monomer, a photoresist composition containing the resin, and a process for manufacturing a semiconductor device using the photoresist composition, in which the monomer is useful as a monomer component of a highly functional polymeric compound, because, when the monomer is derived into a polymeric compound, the polymeric compound is satisfactorily stable and resistant typically to chemicals, is satisfactorily soluble in organic solvents, and can be more satisfactorily hydrolyzable in its ring and/or the hydrolyzed product thereof is more satisfactorily soluble in water. In particular, the monomer having a lactone skeleton according to the present invention has an electron-withdrawing substituent into a polycyclic skeleton including the lactone skeleton, thereby imparts dramatically improved solubility in an alkaline developer to the polymeric compound and thereby enables more finer patterning in the manufacture of semiconductor devices.

BEST MODES FOR CARRYING OUT THE INVENTION

Monomers Having Electron-Withdrawing Substituent and Lactone Skeleton

Monomers according to the present invention having an electron-withdrawing substituent and a lactone skeleton are represented by Formula (1). Examples of the monomers include 6-oxabicyclo[3.2.1$^{1,5}$]octan-7-one derivatives and 3-oxatricyclo[4.2.1.0$^{4,8}$]nonan-2-one derivatives. In Formula (1), $R^a$ represents a hydrogen atom, a halogen atom, or a substituted or unsubstituted alkyl group having 1 to 6 carbon atoms; and $R^1$s are substituents bound to the ring and each represents halogen atom, an alkyl or haloalkyl group having 1 to 6 carbon atoms, a hydroxyalkyl or hydroxyhaloalkyl group having 1 to 6 carbon atoms whose hydroxyl moiety may be protected by a protecting group, a carboxyl group which may form a salt, or a substituted oxycarbonyl group. The ring herein is, for example, 6-oxabicyclo[3.2.1$^{1,5}$]octane ring (when "A" is nonbonding) or 3-oxatricyclo[4.2.1.0$^{4,8}$]nonane ring (i.e., 4-oxatricyclo[4.2.1.0$^{3,7}$]nonane ring) (when "A" is a methylene group). "A" represents an alkylene group having 1 to 6 carbon atoms, an oxygen atom, a sulfur atom, or nonbonding. The symbol "m" is the number of $R^1$s and denotes an integer of 0 to 8. Xs each represent an electron-withdrawing substituent. The symbol "n" is the number of Xs bound to the ring and denotes an integer of 1 to 9. The ring herein is, for example, 6-oxabicyclo[3.2.1$^{1,5}$]octane ring (when "A" is nonbonding) or 3-oxatricyclo[4.2.1.0$^{4,8}$]nonane ring (when "A" is a methylene group). Y represents a bivalent organic group having 1 to 6 carbon atoms. The $CH_2=C(R^a)$ $COO-Y-COO-$ group may have either endo or exo configuration.

In the formula, Xs each represent an electron-withdrawing substituent. Exemplary electron-withdrawing groups include halogen atoms such as fluorine atom; halogenated hydrocarbon groups such as trifluoromethyl group; carboxyl group; alkoxycarbonyl groups such as methoxycarbonyl group; aryloxycarbonyl groups such as phenoxycarbonyl group; acyl groups such as acetyl group; acyloxy groups such as acetoxy group; cyano group; aryl groups; 1-alkenyl groups; nitro group; sulfo group; alkanesulfonyl groups; alkanesulfinyl groups; and alkoxysulfonyl groups. Among them, preferred examples are fluorine-containing groups such as fluorine atom and trifluoromethyl group; acyloxy groups such as acetoxy group; cyano group; nitro group; sulfo group; alkanesulfonyl groups; alkanesulfinyl groups; and alkoxysulfonyl groups, because these groups are highly electron-withdrawing, allow the lactone ring to be highly hydrolyzable, and allow the polymeric compound having the lactone ring to show high solubility in water after hydrolysis.

In Formula (1), exemplary halogen atoms as $R^a$ and $R^1$ include fluorine, chlorine, and bromine atoms. Exemplary alkyl groups having 1 to 6 carbon atoms include methyl, ethyl, propyl, isopropyl, butyl, isobutyl, s-butyl, t-butyl, pentyl, and hexyl groups, of which alkyl groups having 1 to 4 carbon atoms are preferred, and methyl group is especially preferred. Exemplary haloalkyl groups having 1 to 6 carbon atoms include chloroalkyl groups such as chloromethyl group; and fluoroalkyl groups such as trifluoromethyl, 2,2,2-trifluoroethyl, and pentafluoroethyl group (of the fluoroalkyl groups, fluoroalkyl groups having 1 to 3 carbon atoms are preferred). Exemplary substituted alkyl groups having 1 to 6 carbon atoms as $R^a$ include the above-mentioned haloalkyl groups having 1 to 6 carbon atoms.

As R¹, exemplary hydroxyalkyl groups having 1 to 6 carbon atoms include hydroxymethyl, 2-hydroxyethyl, 1-hydroxyethyl, 3-hydroxypropyl, 2-hydroxypropyl, 4-hydroxybutyl, and 6-hydroxyhexyl groups. Exemplary hydroxyhaloalkyl groups having 1 to 6 carbon atoms include difluorohydroxymethyl, 1,1-difluoro-2-hydroxyethyl, 2,2-difluoro-2-hydroxyethyl, and 1,1,2,2-tetrafluoro-2-hydroxyethyl groups. Of the hydroxyalkyl or hydroxyhaloalkyl groups having 1 to 6 carbon atoms, hydroxyalkyl or hydroxyhaloalkyl groups having 1 or 2 carbon atoms are preferred, of which those having one carbon atom are more preferred. Hydroxyl-protecting groups for use in the hydroxyalkyl or hydroxyhaloalkyl groups having 1 to 6 carbon atoms can be protecting groups generally used as hydroxyl-protecting groups in organic syntheses, and examples thereof include methyl group, methoxymethyl group, and other groups which form an ether or acetal bond with oxygen atom constituting the hydroxyl group; and acetyl group, benzoyl group, and other groups which form an ester bond with oxygen atom constituting the hydroxyl group. Exemplary salts of the carboxyl group include alkali metal salts, alkaline earth metal salts, and transition metal salts.

Examples of the substituted oxycarbonyl group include alkoxycarbonyl groups such as methoxycarbonyl, ethoxycarbonyl, isopropyloxycarbonyl, and propoxycarbonyl groups, of which alkoxy-carbonyl groups whose alkoxy moiety having 1 to 4 carbon atoms are preferred; alkenyloxycarbonyl groups such as vinyloxycarbonyl and allyloxycarbonyl groups, of which alkoxy-carbonyl groups whose alkoxy moiety having 2 to 4 carbon atoms are preferred; cycloalkyloxycarbonyl groups such as cyclohexyloxycarbonyl group; and aryloxycarbonyl groups such as phenyloxycarbonyl group.

Preferred examples as $R^a$ include a hydrogen atom; alkyl groups having 1 to 3 carbon atoms, such as methyl group; and haloalkyl groups having 1 to 3 carbon atoms, such as trifluoromethyl group. Among them, $R^a$ is especially preferably a hydrogen atom or methyl group. Preferred examples as R¹s include alkyl groups or haloalkyl groups having 1 to 3 carbon atoms, such as methyl group or trifluoromethyl group; hydroxyalkyl groups or hydroxyhaloalkyl groups having 1 to 3 carbon atoms whose hydroxyl group may be protected, of which protected or unprotected hydroxymethyl groups, such as hydroxymethyl group or acetoxymethyl group, are more preferred; and substituted oxycarbonyl groups.

The number "m" is 0 to 8, preferably 0 to 6, and more preferably 0 to 3. When two or more R¹s are present, they may be the same as or different from one another. The number "n" is 1 to 9, preferably 1 to 5, and more preferably 1 or 2. When two or more Xs are present, they may be the same as or different from one another. Though not critical in position, the electron-withdrawing group X is preferably bound directly to the lactone ring and is more preferably bound directly to the alpha position of the carbonyl group of the lactone ring. As used herein the phrase "bound directly to" refers to that the electron-withdrawing group X is directly bound to a carbon atom consisting the five-membered lactone ring. When the electron-withdrawing group X is bound to the lactone ring with the interposition of one or more atoms, the electron-withdrawing group may not sufficiently exert its activity, and the lactone ring may have insufficient hydrolyzability or the polymeric compound having the lactone ring may have insufficient solubility in water after hydrolysis. When "A" is nonbonding, the substituent X may be bound to any position chosen from the 1-, 2-, 3-, 4-, 5-, and 8-positions of the 6-oxabicyclo[3.2.1$^{1,5}$]octane ring, but is preferably bound to the 1-position (alpha position of the lactone) or 2-position, and is more preferably bound to the 1-position (alpha position of the lactone). When "A" is an alkylene group having 1 to 6 carbon atoms, oxygen atom, or sulfur atom, the substituent X may be bound to any position typically of the 3-oxatricyclo[4.2.1.0$^{4,8}$]nonane ring, such as 1-, 4-, 5-, 6-, 7-, 8-, or 9-position, but is preferably bound to the 1-position or 9-position of the 3-oxatricyclo[4.2.1.0$^{4,8}$]nonane ring (or a position corresponding to these), and is more preferably bound to the 1-position of the 3-oxatricyclo[4.2.1.0$^{4,8}$]nonane ring (or a position corresponding to this; alpha position of the lactone).

"A" represents an alkylene group having 1 to 6 carbon atoms, an oxygen atom, a sulfur atom, or nonbonding. Exemplary alkylene groups having 1 to 6 carbon atoms include alkyl-substituted or unsubstituted methylene groups, alkyl-substituted or unsubstituted ethylene groups, and alkyl-substituted or unsubstituted propylene groups. Above all, "A" is especially preferably an alkylene group having 1 to 6 carbon atoms or nonbonding.

Y represents a bivalent organic group having 1 to 6 carbon atoms. Exemplary bivalent organic groups include methylene, ethylene, propylene, butylene, and other alkylene groups, of which alkylene groups having 1 to 6 carbon atoms are preferred; vinylene and other alkenylene groups, of which alkenylene groups having 2 to 6 carbon atoms are preferred; cyclopentylene, cyclohexylene, and other cycloalkenylene groups; and bivalent organic groups each composed of two or more of these groups bound through a linkage group such as ether bond (—O—), thioether bond (—S—), or ester bond (—COO—; —OCO—). Y is preferably methylene, ethylene, propylene, or a group composed of an alkylene group having 1 to 3 carbon atoms and an alkylene group having 1 or 2 carbon atoms bound with each other through an ester bond. These exemplified groups may be substituted by halogen atoms (of which fluorine atom is preferred), and such substituted groups are also effective herein.

Representative examples of the monomer represented by Formula (1) having an electron-withdrawing substituent and a lactone skeleton include 1-substituted(X)-6-oxabicyclo[3.2.1$^{1,5}$]octan-7-one compounds (including respective stereoisomers), 2-substituted(X)-6-oxabicyclo[3.2.1$^{1,5}$]octan-7-one compounds (including respective stereoisomers), 1-substituted(X)-5-(meth)acryloyloxy-3-oxatricyclo[4.2.1.0$^{4,8}$]nonan-2-one compounds (including respective stereoisomers), and 9-substituted(X)-5-(meth)acryloyloxy-3-oxatricyclo[4.2.1.0$^{4,8}$]nonan-2-one compounds (including respective stereoisomers), represented by the following formulae, and compounds corresponding to these compounds, except that "A" in Formula (1) is another alkylene group than methylene group, oxygen atom, or sulfur atom. In the formulae, R represents a CH$_2$=C(R$^a$)COO—Y—CO— group; Ac represents an acetyl group; and the substituent Xs each represent an electron-withdrawing substituent.

[Chemical Formula 10]

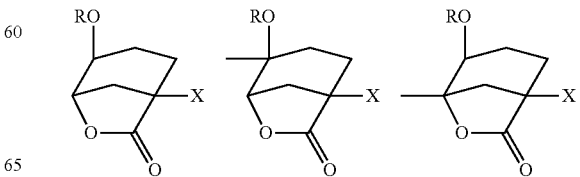

[Chemical Formula 11]

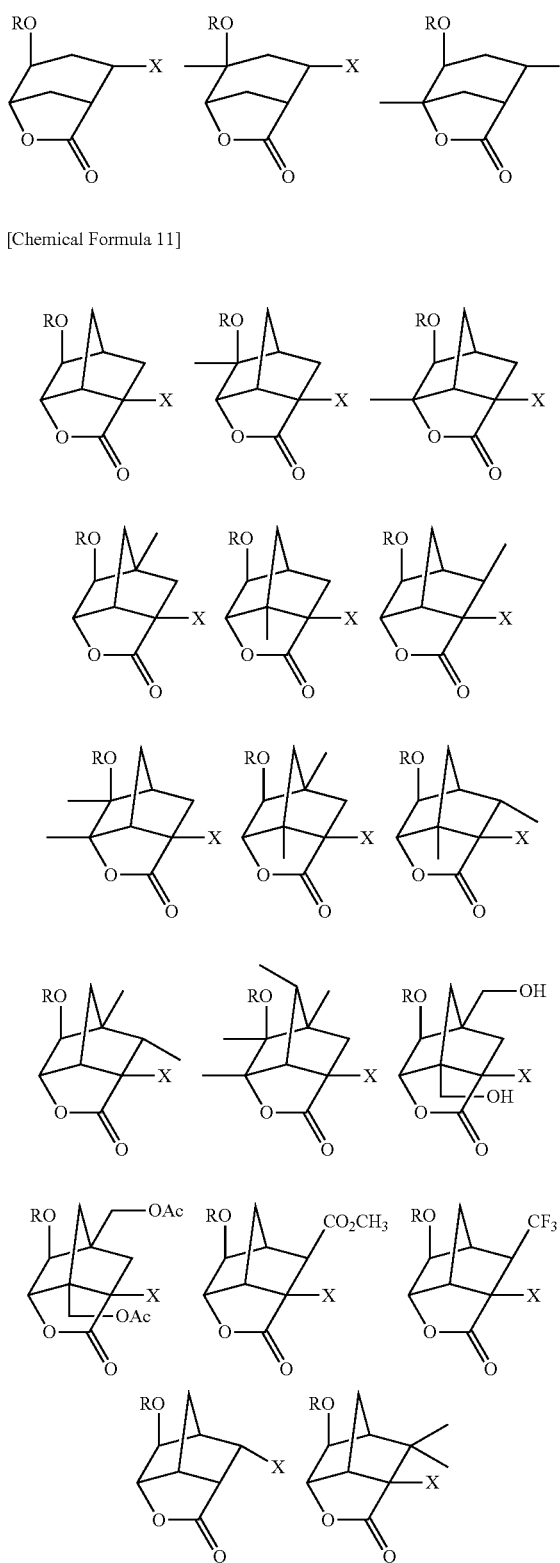

The reaction path of the synthetic preparation of the monomer having an electron-withdrawing substituent and a lactone skeleton, represented by Formula (1), is shown in the following scheme:

[Chemical Formula 12]

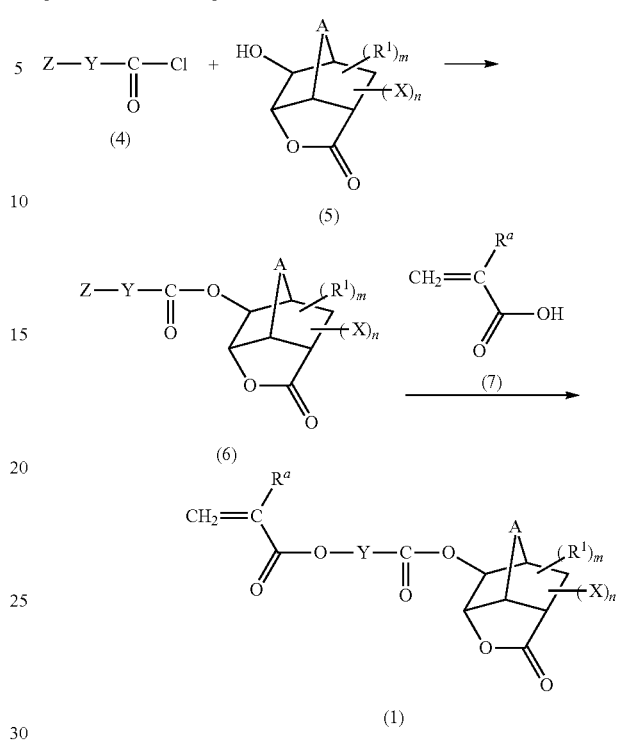

The reaction between a polycyclic alcohol represented by Formula (5) having a lactone skeleton (e.g., a 6-oxabicyclo[3.2.1$^{1,5}$]octan-7-one derivative substituted by X or a 3-oxatricyclo[4.2.1.0$^{4,8}$]nonan-2-one derivative substituted by X) and a carboxylic acid chloride (carbonyl chloride) represented by Formula (4) being substituted by chlorine atom and having a group Y gives an intermediate represented by Formula (6). This reaction is preferably performed in the presence of an organic solvent (e.g., acetonitrile). The reaction is also preferably performed in the presence of an organic base (e.g., pyridine, trialkylamine, or 1,8-diazabicyclo[5.4.0]undec-7-ene (DBU)). The reaction temperature is typically about −30° C. to 100° C. The amount of the compound represented by Formula (4) is typically about 0.8 to 10 moles, per 1 mole of the compound represented by Formula (5).

The resulting intermediate (6) is reacted with an unsaturated carboxylic acid represented by Formula (7) or an alkali metal salt or alkaline earth metal salt thereof [e.g., (meth)acrylic acid] to give a monomer (1) having an electron-withdrawing substituent and a lactone skeleton. This reaction is preferably performed in the state of a solution or suspension in an organic solvent (e.g., N,N-dimethylformamide). The reaction gives hydrogen chloride as a by-product, and the reaction is therefore preferably performed in the presence of a base so as to carry out dehydrochlorination. Exemplary bases include carbonates or hydrogen carbonates of alkali metals, such as potassium carbonate, sodium carbonate, and sodium hydrogen carbonate. It is also desirable to perform the reaction in the presence of a halogen-exchange agent. Exemplary halogen-exchange agents include alkali metal halides such as sodium iodide, potassium iodide, sodium bromide, and potassium bromide. The reaction temperature is typically about −10° C. to 100° C. Each of different unsaturated carboxylic acids, alkali metal salts and alkaline earth metal salts thereof, may be used alone or in combination. The total amount of the unsaturated carboxylic acids represented by Formula (7) and alkali metal salts and alkaline earth metal salts thereof is typically about 0.8 to 10 moles and preferably about 1 to 2 moles, per 1 mole of the compound represented by Formula (6).

As $R^a$ in Formula (7), exemplary halogen atoms include fluorine, chlorine, and bromine atoms. Exemplary substituted alkyl groups having 1 to 6 carbon atoms as $R^a$ include methyl, ethyl, propyl, isopropyl, butyl, isobutyl, s-butyl, t-butyl, pentyl, and hexyl groups, of which alkyl groups having 1 to 4 carbon atoms are preferred, and methyl group is more preferred. Exemplary haloalkyl groups having 1 to 6 carbon atoms include chloroalkyl groups such as chloromethyl group; and fluoroalkyl groups such as trifluoromethyl, 2,2,2-trifluoroethyl, and pentafluoroethyl groups (of which fluoroalkyl groups having 1 to 3 carbon atoms are preferred). Exemplary alkali metals as M in Formula (7) include lithium, sodium, and potassium. Exemplary alkaline earth metals as M include beryllium, magnesium, and calcium.

Representative examples of alkali metal salts of the unsaturated carboxylic acid represented by Formula (7) include sodium methacrylate and sodium acrylate. Representative examples of alkaline earth metal salts of the unsaturated carboxylic acid represented by Formula (7) include magnesium methacrylate and magnesium acrylate.

Z represents chlorine, bromine, or iodine. Among them, iodine and bromine are more preferred for their higher reactivity. The compound represented by Formula (1) (the monomer having an electron-withdrawing substituent and a lactone skeleton) can be produced herein through the intermediate (6). In this case, the reaction may be performed by using the intermediate halogen-containing lactone compound represented by Formula (6) as intact without any treatment or may be performed while carrying out halogen exchange in the reaction system and whereby converting the compound represented by Formula (6) into a corresponding higher-reactive bromine- or iodine-containing lactone.

Each of the intermediate represented by Formula (6) and the compound represented by Formula (1) (the monomer having an electron-withdrawing substituent and a lactone skeleton) formed as a result of reactions can be separated and purified through a separation process such as filtration, concentration, distillation, extraction, crystallization, recrystallization, or column chromatography, or any combination of these separation processes.

The compound represented by Formula (5) can be prepared according typically to the following reaction scheme:

[Chemical Formula 13]

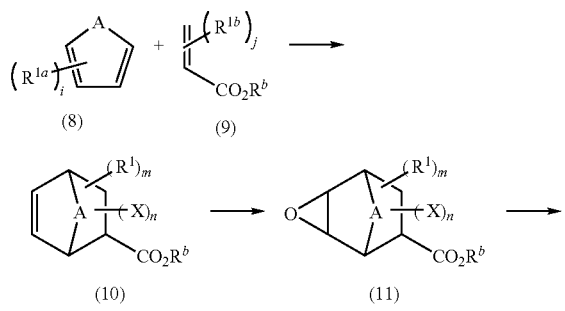

-continued

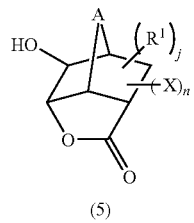

(5)

In the scheme, $R^{1a}$s are substituents bound to the diene chain or cyclopentadiene ring and each represent a halogen atom, an alkyl or haloalkyl group having 1 to 6 carbon atoms, a hydroxyalkyl or hydroxyhaloalkyl group having 1 to 6 carbon atoms whose hydroxyl moiety may be protected by a protecting group, a carboxyl group which may form a salt, a substituted oxycarbonyl group, or an electron-withdrawing substituent. $R^{1b}$s are substituents bound to a carbon atom constituting the carbon-carbon double bond and each represent a halogen atom, an alkyl or haloalkyl group having 1 to 6 carbon atoms, a hydroxyalkyl or hydroxyhaloalkyl group having 1 to 6 carbon atoms whose hydroxyl moiety may be protected by a protecting group, a carboxyl group which may form a salt, a substituted oxycarbonyl group, or an electron-withdrawing substituent. $R^b$ represents a hydrogen atom or an organic group (e.g., an alkyl group having 1 to 4 carbon atoms, such as methyl group). The symbol "i" is the number of $R^{1a}$s and denotes an integer of 0 to 6. The symbol "j" is the number of $R^{1b}$s and denotes an integer of 0 to 3. At least one of $iR^{1a}$s and $jR^{1b}$s is an electron-withdrawing substituent. "A" and X are as defined above. $R^1$, "m", and "n" are as defied above, and concrete examples and preferred examples (ranges) of them are also as described above. It is preferred that at least one of $jR^{1b}$s in Formula (9) is an electron-withdrawing substituent; and it is more preferred that the electron-withdrawing substituent is bound to the alpha position of the —$CO_2R^b$ group.

More specifically, the compound represented by Formula (5) can be prepared by subjecting a diene compound represented by Formula (8) (e.g., a butadiene or cyclopentadiene derivative) and an unsaturated carboxylic acid or an ester thereof represented by Formula (9) to a Diels-Alder reaction to give a cycloadduct represented by Formula (10) (e.g., a cyclohexene derivative or bicyclo[2.2.1]hept-2-ene derivative); reacting the cycloadduct with a peracid or peroxide to give an epoxy compound represented by Formula (11) (e.g., a cyclohexene oxide derivative or 2,3-epoxybicyclo[2.2.1]heptane derivative); and subjecting the epoxy compound to a cyclization reaction. Typically when $R^b$ is a hydrogen atom, the compound represented by Formula (10) may be reacted with a peracid or peroxide so as to induce cyclization immediately after epoxidation to give the compound represented by Formula (5) as a main product.

Representative examples of diene compounds represented by Formula (8) (e.g., butadienes or cyclopentadiene derivatives) include butadiene, isoprene, 1,3-cyclopentadiene, 1-methyl-1,3-cyclopentadiene, 2-methyl-1,3-cyclopentadiene, 5-methyl-1,3-cyclopentadiene, 1,2-dimethyl-1,3-cyclopentadiene, 1,4-dimethyl-1,3-cyclopentadiene, 2,3-dimethyl-1,3-cyclopentadiene, 1,2,3,4-tetramethyl-1,3-cyclopentadiene, 1,2,3,4,5-pentamethyl-1,3-cyclopentadiene, 1-hydroxymethyl-1,3-pentadiene, 1,4-bis(hydroxymethyl)-1,3-cyclopentadiene, 2,3-bis(hydroxymethyl)-1,3-cyclopentadiene, 1-acetoxymethyl-1,3-cyclopentadiene, 1,4-bis(acetoxymethyl)-1,3-cyclopentadiene, and 2,3-bis(acetoxymethyl)-1,3- cyclopentadiene. Representative examples of diene compounds represented by Formula (8), in which "A" is oxygen atom or sulfur atom, include furan, 2-methylfuran, 3-methylfuran, 2,3-dimethylfuran, thiophene, 2-methylthiophene, 3-methylthiophene, and 2,3-dimethylthiophene.

The reaction between the compound represented by Formula (8) and the compound represented by Formula (9) is performed in the presence of, or in the absence of, a solvent (e.g., toluene). A Lewis acid (e.g., $AlCl_3$) may be present in the reaction system to improve the reaction rate and reaction selectivity (such as stereoselectivity). The reaction temperature is typically about −70° C. to 250° C.

Of peracids or peroxides to be reacted with the compound represented by Formula (10), exemplary peracids include peracetic acid, perbenzoic acid, and m-chloroperbenzoic acid. The amount of peracids is typically about 0.8 to 2 moles and preferably about 0.9 to 1.5 moles, per 1 mole of the compound represented by Formula (10).

Exemplary peroxides to be reacted with the compound represented by Formula (10) include hydrogen peroxide, other peroxides, hydroperoxides, peroxoacids, and salts of peroxoacids. The amount of peroxides (e.g., hydrogen peroxide) is typically about 0.9 to 5 moles and preferably about 0.9 to 3 moles, per 1 mole of the compound represented by Formula (10).

The hydrogen peroxide is often used in combination with a metallic compound. Examples of the metallic compound include oxides, oxoacids or salts thereof, and peroxides each containing one or more metal elements such as tungsten (W), molybdenum (Mo), vanadium (V), manganese (Mn), and rhenium (Re). Each of these metallic compounds can be used alone or in combination. Exemplary oxides include tungsten oxides, molybdenum oxides, vanadium oxides, manganese oxides, and multicomponent oxides containing metal elements such as W, Mo, V, and Mn. Exemplary oxoacids include tungstic acid, molybdic acid, vanadic acid, and manganic acid; as well as isopolyacids, and heteropolyacids. Exemplary salts of oxoacids include alkali metal salts, alkaline earth metal salts, ammonium salts, and transition metal salts, of the oxoacids. Exemplary peroxides containing metal elements include peroxoacids such as peroxotungstic acid, peroxomolybdic acid, and peroxovanadic acid; salts of peroxoacids, such as alkali metal salts, alkaline earth metal salts, ammonium salts, and transition metal salts, of the peroxoacids; peracids such as permanganic acid; and salts of peracids, such as alkali metal salts, alkaline earth metal salts, ammonium salts, and transition metal salts, of the peracids. The amount of the metallic compounds used in combination with hydrogen peroxide is typically about 0.0001 to 2 moles and preferably about 0.0005 to 0.5 moles, per 1 mole of the compound represented by Formula (10).

The reaction between the compound represented by Formula (10) and the peracid or peroxide is performed in the presence of, or in the absence of, a solvent such as methylene chloride or water. The reaction temperature is generally about −10° C. to 100° C., and preferably about 0° C. to 80° C. The reaction induces the epoxidation of the double bond in the compound represented by Formula (10) to give an epoxy compound represented by Formula (11). As has been described above, typically when $R^b$ is a hydrogen atom, an intramolecular cyclization reaction accompanied by ring-opening of epoxy ring may subsequently proceed to give a polycyclic alcohol represented by Formula (5) having an electron-withdrawing substituent and a lactone skeleton.

When $R^b$ is a hydrogen atom, the cyclization reaction of the compound represented by Formula (11) proceeds, for example, merely by dissolving the compound represented by Formula (11) in a solvent. When $R^b$ is an organic group, once the compound represented by Formula (11) is subjected to a common hydrolysis reaction to be converted into a corresponding compound where $R^b$ is a hydrogen atom, the cyclization reaction immediately proceeds to give the compound represented by Formula (5). Exemplary hydrolysis reactions include hydrolysis reaction with an alkali, hydrolysis reaction with an acid, and neutral hydrolysis.

Each of the compound represented by Formula (10), the compound represented by Formula (11), and the compound represented by Formula (5) formed as a result of reactions can be separated and purified according to a separation process such as filtration, concentration, distillation, extraction, crystallization, recrystallization, or column chromatography, or any combination of these separation processes.

[Polymeric Compounds]

Polymeric compounds according to the present invention each include a monomeric unit (constitutional repeating unit) corresponding to the monomer represented by Formula (1) having an electron-withdrawing substituent and a lactone skeleton. Specifically, the polymeric compounds include a monomeric unit represented by Formula (1). The polymeric compounds may include one or more kinds of such monomeric unit. The polymeric compounds can be obtained by subjecting the monomer represented by Formula (1) having an electron-withdrawing substituent and a lactone skeleton to polymerization.

The monomeric unit represented by Formula (I) has, for example, a 6-oxabicyclo[3.2.1$^{1,5}$]octan-7-one skeleton with an electron-withdrawing substituent bound thereto, or a 3-oxatricyclo[4.2.1.0$^{4,8}$]nonan-2-one skeleton with an electron-withdrawing substituent bound thereto. This monomeric unit gives a polymer in which the lactone ring constituting part typically of the 6-oxabicyclo[3.2.1$^{1,5}$]octan-7-one skeleton or 3-oxatricyclo[4.2.1.0$^{4,8}$]nonan-2-one skeleton is more liable to be hydrolyzed, and this monomeric unit also gives a polymer that is more soluble in water after hydrolysis, than a unit having a 6-oxabicyclo[3.2.1$^{1,5}$]octan-7-one skeleton without an electron-withdrawing substituent or a unit having a 3-oxatricyclo[4.2.1.0$^{4,8}$]nonan-2-one skeleton without an electron-withdrawing substituent does. Accordingly, the polymeric compounds according to the present invention are useful as highly functional polymers adopted typically to applications in which the function of being converted to be soluble in water through a predetermined treatment is required. The polymeric compounds are particularly useful as photoresist resins.

The polymeric compounds according to the present invention may further include one or more other monomeric units in addition to the monomeric unit represented by Formula (I), in accordance with the intended use and required functions. Such other monomeric units can be formed by copolymerizing polymerizable unsaturated monomers corresponding to the other monomeric units with the monomer represented by Formula (1) having an electron-withdrawing substituent and a lactone skeleton.

Examples of the other monomeric units include monomeric units part of which will leave with an acid to allow the polymeric compound to be soluble in an alkali, such as monomeric units represented by Formulae (IIa), (IIb), (IIc), and (IId). Polymerizable unsaturated monomers corresponding to the monomeric units represented by Formulae (IIa), (IIb), (IIc), and (IId) are respectively represented by following Formula (2a), (2b), (2c), and (2d):

[Chemical Formula 14]

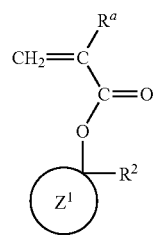

(2a)

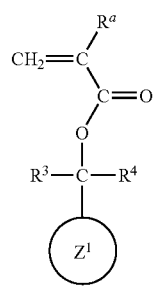

(2b)

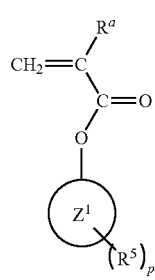

(2c)

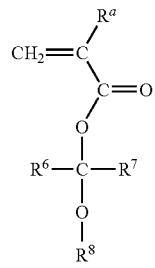

(2d)

In the above formulae, Ring $Z^1$ represents a substituted or unsubstituted alicyclic hydrocarbon ring having 5 to 20 carbon atoms. $R^a$ is as defined above. $R^2$, $R^3$, and $R^4$ are the same as or different from one another and each represent a substituted or unsubstituted alkyl group having 1 to 6 carbon atoms. $R^5$s are substituents bound to Ring $Z^1$, are the same as or different from each other, and each represent an oxo group, an alkyl group, a protected or unprotected hydroxyl group, a protected or unprotected hydroxyalkyl group, or a protected or unprotected carboxyl group, wherein at least one of p$R^5$s represents a —COOR$^c$ group, in which R$^c$ represents a substituted or unsubstituted tertiary hydrocarbon group, a tetrahydrofuranyl group, a tetrahydropyranyl group, or an oxepanyl group. The symbol "p" denotes an integer of 1 to 3. $R^6$ and $R^2$ are the same as or different from each other and each represent a hydrogen atom or a substituted or unsubstituted alkyl group having 1 to 6 carbon atoms; and $R^8$ represents a hydrogen atom or an organic group, wherein at least two of $R^6$, $R^7$, and $R^8$ may be bound to each other to form a ring with an adjacent atom.

In Formulae (2a), (2b), and (2c), the alicyclic hydrocarbon ring having 5 to 20 carbon atoms as Ring $Z^2$ may be a monocyclic ring or a polycyclic ring such as fused ring or bridged ring. Representative examples of the alicyclic hydrocarbon ring include cyclohexane ring, cyclooctane ring, cyclodecane ring, adamantane ring, norbornane ring, norbornene ring, bornane ring, isobornane ring, perhydroindene ring, decahydronaphthalene ring, perhydrofluorene ring (tricyclo[7.4.0.0$^{3,8}$]tridecane ring), perhydroanthracene ring, tricyclo[5.2.1.0$^{2,6}$]decane ring, tricyclo[4.2.2.1$^{2,5}$]undecane ring, and tetracyclo[4.4.0.1$^{2,5}$.1$^{7,10}$]dodecane ring. The alicyclic hydrocarbon ring may have one or more substituents. Exemplary substituents include methyl group and other alkyl groups (e.g., alkyl groups having 1 to 4 carbon atoms); chlorine atom and other halogen atoms; protected or unprotected hydroxyl groups; oxo groups; and protected or unprotected carboxyl groups. Ring $Z^1$ is preferably a polycyclic alicyclic hydrocarbon ring (bridged hydrocarbon ring) such as adamantane ring.

Exemplary substituted or unsubstituted alkyl groups having 1 to 6 carbon atoms as $R^2$, $R^3$, $R^4$, $R^6$, and $R^7$ in Formulae (2a), (2b), and (2d) include linear or branched-chain alkyl groups having 1 to 6 carbons, such as methyl, ethyl, propyl, isopropyl, butyl, isobutyl, s-butyl, t-butyl, and hexyl groups; haloalkyl groups having 1 to 6 carbons, such as trifluoromethyl group. Exemplary alkyl groups as $R^5$s in Formula (2c) include linear or branched-chain alkyl groups having about 1 to 20 carbons, such as methyl, ethyl, propyl, isopropyl, butyl, isobutyl, s-butyl, t-butyl, hexyl, octyl, decyl, and dodecyl groups. Exemplary protected or unprotected hydroxyl groups as $R^5$s include hydroxyl group; and substituted oxy groups including alkoxy groups having 1 to 4 carbon atoms, such as methoxy, ethoxy, and propoxy groups. Exemplary protected or unprotected hydroxyalkyl groups include groups each composed of an alkylene group having 1 to 6 carbon atoms bound to the protected or unprotected hydroxyl group. Exemplary protected or unprotected carboxyl groups include —COOR$^d$ groups, in which R$^d$ represents a hydrogen atom or an alkyl group, and examples of the alkyl group include linear or branched-chain alkyl groups having 1 to 6 carbon atoms, such as methyl, ethyl, propyl, isopropyl, butyl, isobutyl, s-butyl, t-butyl, and hexyl groups. Exemplary tertiary hydrocarbon groups as R$^c$ in the —COOR$^c$ group as $R^5$ include t-butyl, t-amyl, 2-methyl-2-adamantyl, and (1-methyl-1-adamantyl) ethyl groups. Exemplary tetrahydrofuranyl groups include 2-tetrahydrofuranyl group; exemplary tetrahydropyranyl groups include 2-tetrahydropyranyl group; and exemplary oxepanyl groups include 2-oxepanyl group.

Exemplary organic groups as $R^8$ include groups each containing a hydrocarbon group and/or a heterocyclic group. Exemplary hydrocarbon groups include aliphatic hydrocarbon groups, alicyclic hydrocarbon groups, aromatic hydrocarbon groups, and groups each composed of two or more of these bound with each other. Exemplary aliphatic hydrocarbon groups include linear or branched-chain alkyl groups such as methyl, ethyl, propyl, isopropyl, butyl, isobutyl, s-butyl, t-butyl, hexyl, and octyl groups, of which alkyl groups having 1 to 8 carbon atoms are preferred; linear or branched-chain alkenyl groups such as allyl group, of which alkenyl groups having 2 to 8 carbon atoms are preferred; and linear or branched-chain alkynyl groups such as propynyl group, of which alkynyl groups having 2 to 8 carbon atoms are preferred. Exemplary alicyclic hydrocarbon groups include cycloalkyl groups such as cyclopropyl, cyclopentyl, and cyclohexyl groups, of which cycloalkyl groups having 3 to 8 members are preferred; cycloalkenyl groups such as cyclopentenyl and cyclohexenyl groups, of which cycloalkenyl groups having 3 to 8 members are preferred; and bridged carbocyclic groups such as adamantyl and norbornyl groups, of which bridged carbocyclic groups having 4 to 20 carbon atoms are preferred. Exemplary aromatic hydrocarbon groups include aromatic hydrocarbon groups having 6 to 14 carbon atoms, such as phenyl and naphthyl groups. Exemplary groups each composed of an aliphatic hydrocarbon group and an aromatic hydrocarbon group bound to each other include benzyl and 2-phenylethyl groups. These hydrocarbon groups may each have one or more substituents. Exemplary substituents include alkyl groups such as alkyl groups having 1 to 4 carbon atoms; haloalkyl groups such as haloalkyl groups having 1 to 4 carbon atoms; halogen atoms; protected or unprotected hydroxyl groups; protected or unprotected hydroxymethyl groups; protected or unprotected carboxyl groups; and oxo groups. As the protecting groups herein, protecting groups commonly used in organic syntheses are usable.

Examples of the heterocyclic groups include heterocyclic groups each containing at least one heteroatom selected from the group consisting of oxygen atom, sulfur atom, and nitrogen atom.

Preferred examples of the organic group include alkyl groups having 1 to 8 carbon atoms, and organic groups each having a cyclic skeleton. Exemplary "rings" constituting the cyclic skeleton include monocyclic or polycyclic, nonaromatic or aromatic carbocycles or heterocycles. Among them, monocyclic or polycyclic nonaromatic carbocycles and lactone rings (to which a nonaromatic carbocycle may be fused) are more preferred. Exemplary monocyclic nonaromatic carbocycles include cycloalkane rings having about 3 to 15 members, such as cyclopentane ring and cyclohexane ring.

Exemplary polycyclic nonaromatic carbocycles (bridged carbocycles) include adamantane ring; rings containing a norbornane ring or norbornene ring, such as norbornane ring, norbornene ring, bornane ring, isobornane ring, tricyclo[5.2.1.0$^{2,6}$]decane ring, and tetracyclo[4.4.0.1$^{2,5,7,10}$]dodecane ring; rings corresponding to polycyclic aromatic fused rings, except for being hydrogenated, such as perhydroindene ring, decahydronaphthalene ring (perhydronaphthalene ring), perhydrofluorene ring (tricyclo[7.4.0.0$^{3,8}$]tridecane ring), and perhydroanthracene ring, of which fully hydrogenated rings are preferred; and bridged carbocycles each containing, for example, two, three, or four rings, such as tricyclo[4.2.2.1$^{2,5}$]undecane ring, of which bridged carbocyclic rings having about 6 to 20 carbon atoms are preferred. Examples of the lactone rings include γ-butyrolactone ring, 4-oxatricyclo[4.3.1.1$^{3,8}$]undecan-5-one ring, 3-oxatricyclo[4.2.1.0$^{4,8}$]nonan-2-one ring, and 4-oxatricyclo[5.2.1.0$^{2,6}$]decan-5-one ring.

The ring constituting the cyclic skeleton may have one or more substituents. Exemplary substituents include alkyl groups such as methyl group, of which alkyl groups having 1 to 4 carbon atoms are preferred; haloalkyl groups such as trifluoromethyl group, of which haloalkyl groups having 1 to 4 carbon atoms are preferred; halogen atoms such as chlorine atom and fluorine atom; protected or unprotected hydroxyl groups; protected or unprotected hydroxyalkyl groups; protected or unprotected mercapto groups; protected or unprotected carboxyl groups; protected or unprotected amino groups; and protected or unprotected sulfonic groups. As the protecting groups herein, protecting groups commonly used in organic syntheses are usable.

The ring constituting the cyclic skeleton may be bound to the oxygen atom in Formula (2d) (oxygen atom at the adjacent position to R$^8$) directly or indirectly through a linkage group. Exemplary linkage groups include linear or branched-chain alkylene groups such as methylene, methylmethylene, dimethylmethylene, ethylene, propylene, and trimethylene groups; carbonyl group; oxygen atom (ether bond; —O—); oxycarbonyl group (ester bond; —COO—); aminocarbonyl group (amide bond; —CONH—); and groups each composed of two or more of these bound to each other.

At least two of R$^6$, R$^7$, and R$^8$ may be bound to each other to form a ring with an adjacent atom. Examples of the ring include cycloalkane rings such as cyclopropane ring, cyclopentane ring, and cyclohexane ring; oxygen-containing rings such as tetrahydrofuran ring, tetrahydropyran ring, and oxepane ring; and bridged rings.

There can be stereoisomers in compounds represented by Formulae (2a), (2b), (2c), and (2d), respectively. Each of such stereoisomers can be used alone or in combination as a mixture.

Representative examples of the compound represented by Formula (2a) include, but are not limited to, 2-(meth)acryloyloxy-2-methyladamantane, 1-hydroxy-2-(meth)acryloyloxy-2-methyladamantane, 5-hydroxy-2-(meth)acryloyloxy-2-methyladamantane, and 2-(meth)acryloyloxy-2-ethyladamantane.

Representative examples of the compound represented by Formula (2b) include, but are not limited to, 1-(1-(meth)acryloyloxy-1-methylethyl)adamantane, 1-hydroxy-3-(1-(meth)acryloyloxy-1-methylethyl)adamantane, 1-(1-ethyl-1-(meth)acryloyloxypropyl)adamantane, 1-(1-(meth)acryloyloxy-1-methylpropyl)adamantane, and 1-(1-methacryloyloxy-1-methylethyl)cyclohexane.

Representative examples of the compound represented by Formula (2c) include, but are not limited to, 1-t-butoxycarbonyl-3-(meth)acryloyloxyadamantane and 1-(2-tetrahydropyranyloxycarbonyl)-3-(meth)acryloyloxyadamantane.

Representative examples of the compound represented by Formula (2d) include, but are not limited to, 1-adamantyloxy-1-ethyl(meth)acrylates, 1-adamantylmethyloxy-1-ethyl(meth)acrylates, 2-(1-adamantylethyl)oxy-1-ethyl(meth)acrylates, 1-bornyloxy-1-ethyl(meth)acrylates, 2-norbornyloxy-1-ethyl(meth)acrylates, 2-tetrahydropyranyl(meth)acrylates, and 2-tetrahydrofuranyl(meth)acrylates.

The compound represented by Formula (2d) can be obtained, for example, by reacting a corresponding vinyl ether compound with (meth)acrylic acid according to customary processes. Typically, 1-adamantyloxy-1-ethyl(meth)acrylate can be prepared by reacting 1-adamantyl-vinyl-ether with (meth)acrylic acid in the presence of an acid catalyst.

Examples of the other monomeric units further include, in addition to those mentioned above, monomeric units that can impart or improve properties such as hydrophilicity and/or solubility in water. Exemplary monomers corresponding to the monomeric units just mentioned above include polar-group-containing monomers such as hydroxyl-containing monomers (including hydroxyl-protected compounds), mercapto-containing monomers (including mercapto-protected compounds), carboxyl-containing monomers (including carboxyl-protected compounds), amino-containing monomers (including amino-protected compounds), sulfonic-containing monomers (including sulfonic-protected compounds), lactone-skeleton-containing monomers, cyclic-ketone-skeleton-containing monomers, acid-anhydride-containing monomers, imide-containing monomers, and other monomers.

Examples of the other monomeric units include monomeric units containing an alicyclic skeleton having at least one substituent, such as monomeric units represented by Formula (III). Polymerizable unsaturated monomers corresponding to the monomeric units represented by Formula (III) are represented by following Formula (3):

[Chemical Formula 15]

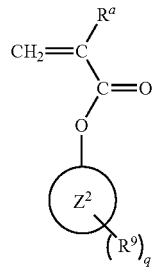

(3)

In the formula, Ring $Z^2$ represents an alicyclic hydrocarbon ring having 6 to 20 carbon atoms. $R^a$ is as defined above. $R^9$s are substituents bound to Ring $Z^2$, are the same as or different from each other, and each represent an oxo group, an alkyl group, a haloalkyl group, a halogen atom, a protected or unprotected hydroxyl group, a protected or unprotected hydroxyalkyl group, a protected or unprotected mercapto group, a protected or unprotected carboxyl group, a protected or unprotected amino group, or a protected or unprotected sulfonic group. The symbol "q" is the number of $R^9$s and denotes an integer of 1 to 5.

Of the monomers represented by Formula (3), monomers in which at least one of $qR^9$s is an oxo group, a protected or unprotected hydroxyl group, a protected or unprotected hydroxyalkyl group, a protected or unprotected mercapto group, a protected or unprotected carboxyl group, a protected or unprotected amino group, or a protected or unprotected sulfonic group correspond to the polar-group-containing monomers that can impart hydrophilicity and/or solubility in water to the polymer or improve the hydrophilicity and/or solubility of the polymer.

The alicyclic hydrocarbon ring having 6 to 20 carbon atoms as Ring $Z^2$ may be a monocyclic ring or a polycyclic ring such as bridged ring. Representative alicyclic hydrocarbon rings include cyclohexane ring, cyclooctane ring, cyclodecane ring, adamantane ring, norbornane ring, norbornene ring, bornane ring, isobornane ring, perhydroindene ring, decahydronaphthalene ring, perhydrofluorene ring (tricyclo[7.4.0.0$^{3,8}$]tridecane ring), perhydroanthracene ring, tricyclo[5.2.1.0$^{2,6}$]decane ring, tricyclo[4.2.2.1$^{2,5}$]undecane ring, and tetracyclo[4.4.0.1$^{2,5}$.1$^{7,10}$]dodecane ring. Of the alicyclic hydrocarbon rings, bridged alicyclic hydrocarbon rings such as adamantane ring are especially preferred.

As $R^9$s in Formula (3), exemplary alkyl groups include linear or branched-chain alkyl groups having about 1 to 20 carbon atoms, such as methyl, ethyl, propyl, isopropyl, butyl, isobutyl, s-butyl, t-butyl, hexyl, octyl, decyl, and dodecyl groups, of which alkyl groups having 1 to 4 carbon atoms are preferred. Exemplary haloalkyl groups include haloalkyl groups having about 1 to 20 carbon atoms, such as trifluoromethyl group, of which haloalkyl groups having 1 to 4 carbon atoms are preferred. Exemplary halogen atoms include fluorine atom and chlorine atom. Exemplary protected or unprotected amino groups include amino group; and substituted amino groups including alkylamino groups having 1 to 4 carbon atoms, such as methylamino, ethylamino, and propylamino groups. Exemplary protected or unprotected sulfonic groups include —SO$_3$R$^e$ groups. The substituent R$^e$ represents a hydrogen atom or an alkyl group, and exemplary alkyl groups herein include linear or branched-chain alkyl groups having 1 to 6 carbon atoms, such as methyl, ethyl, propyl, isopropyl, butyl, isobutyl, s-butyl, t-butyl, and hexyl groups. The protected or unprotected hydroxyl group, protected or unprotected hydroxyalkyl group, protected or unprotected mercapto group, and protected or unprotected carboxyl group as $R^9$s are as described above.

Representative examples of the compounds represented by Formula (3) include, but are not limited to, 1-hydroxy-3-(meth)acryloyloxyadamantane, 1,3-dihydroxy-5-(meth)acryloyloxyadamantane, 1-carboxy-3-(meth)acryloyloxyadamantane, 1,3-dicarboxy-5-(meth)acryloyloxyadamantane, 1-carboxy-3-hydroxy-5-(meth)acryloyloxyadamantane, 1-t-butoxycarbonyl-3-(meth)acryloyloxyadamantane, 1,3-bis(t-butoxycarbonyl)-5-(meth)acryloyloxyadamantane, 1-t-butoxycarbonyl-3-hydroxy-5-(meth)acryloyloxyadamantane, 1-(2-tetrahydropyranyloxycarbonyl)-3-(meth)acryloyloxyadamantane, 1,3-bis(2-tetrahydropyranyloxycarbonyl)-5-(meth)acryloyloxyadamantane, 1-hydroxy-3-(2-tetrahydropyranyloxycarbonyl)-5-(meth)acryloyloxyadamantane, and 1-(meth)acryloyloxy-4-oxoadamantane.

Monomers containing an alicyclic skeleton (e.g., adamantane skeleton) having at least one substituent selected from hydroxyl group and hydroxymethyl group are preferred as the monomers corresponding to the monomeric units containing an alicyclic skeleton having at least one substituent.

Examples of the other monomeric units further include monomeric units having a lactone skeleton [other than the monomeric units represented by Formula (I)]. Specific examples of polymerizable unsaturated monomers [lactone-ring-containing monomers (other than the compounds represented by Formula (I))] corresponding to the monomeric units having a lactone skeleton [other than the monomeric units represented by Formula (I)] include the following compounds.

1-(Meth)acryloyloxy-4-oxatricyclo[4.3.1.1$^{3,8}$]undecan-5-one, 1-(meth)acryloyloxy-4,7-dioxatricyclo[4.4.1.1$^{3,9}$]dodecane-5,8-dione, 1-(meth)acryloyloxy-4,8-dioxatricyclo[4.4.1.1$^{3,9}$]dodecane-5,7-dione, 1-(meth)acryloyloxy-5,7-dioxatricyclo[4.4.1.1$^{3,9}$]dodecane-4,8-dione, 5-(meth)acryloyloxy-3-oxatricyclo[4.2.1.0$^{4,8}$]nonan-2-one, 5-(meth)acryloyloxy-5-methyl-3-oxatricyclo[4.2.1.0$^{4,8}$]nonan-2-one, 5-(meth)acryloyloxy-6-methyl-3-oxatricyclo[4.2.1.0$^{4,8}$]nonan-2-one, 5-(meth)acryloyloxy-9-methyl-3-oxatricyclo[4.2.1.0$^{4,8}$]nonan-2-one, 5-(meth)acryloyloxy-9-carboxy-3-oxatricyclo[4.2.1.0$^{4,8}$]nonan-2-one, 5-(meth)acryloyloxy-9-methoxycarbonyl-3-oxatricyclo[4.2.1.0$^{4,8}$]nonan-2-one, 5-(meth)acryloyloxy-9-ethoxycarbonyl-3-oxatricyclo[4.2.1.0$^{4,8}$]nonan-2-one, 5-(meth)acryloyloxy-9-(t-butoxy)carbonyl-3-oxatricyclo[4.2.1.0$^{4,8}$]nonan-5-one, 8-(meth)acryloyloxy-4-oxatricyclo[5.2.1.0$^{2,6}$]decan-5-one, 9-(meth)acryloyloxy-4-oxatricyclo[5.2.1.0$^{2,6}$]decan-5-one, 4-(meth)acryloyloxy-6-oxabicyclo[3.2.1]octan-7-one, 4-(meth)acryloyloxy-4-methyl-6-oxabicyclo[3.2.1]octan-7-one, 4-(meth)acryloyloxy-5-methyl-6-oxabicyclo[3.2.1]octan-7-one, 4-(meth)acryloyloxy-4,5-dimethyl-6-oxabicyclo[3.2.1]octan-7-one, 6-(meth)acryloyloxy-2-oxabicyclo[2.2.2]octan-3-one, 6-(meth)acryloyloxy-6-methyl-2-oxabicyclo[2.2.2]octan-3-one, 6-(meth)acryloyloxy-1-methyl-2-oxabicyclo[2.2.2]octan-3-one, 6-(meth)acryloyloxy-1,6-dimethyl-2-oxabicyclo[2.2.2]octan-3-one, β-(meth)acryloyloxy-γ-butyrolactone, β-(meth)acryloyloxy-α,α-dimethyl-γ-butyrolactone, β-(meth)acryloyloxy-γ,γ-dimethyl-γ-butyrolactone, β-(meth)acryloyloxy-α,α,β-trimethyl-γ-butyrolactone, β-(meth)acryloyloxy-β,γ,γ-trimethyl-γ-butyrolactone, β-(meth)acryloyloxy-α,α,β,γ,γ-pentamethyl-γ-butyrolactone, α-(meth)acryloyloxy-γ-butyrolactone, α-(meth)acryloyloxy-α-methyl-γ-butyrolactone, α-(meth)acryloyloxy-β,β-dimethyl-γ-butyrolactone, α-(meth)acryloyloxy-α,β,β-trimethyl-γ-butyrolactone, α-(meth)acryloyloxy-γ,γ-dimethyl-γ-butyrolactone, α-(meth)acryloyloxy-α,γ,γ-trimethyl-γ-butyrolactone, α-(meth)acryloyloxy-β,β,γ,γ-tetramethyl-γ-butyrolactone, and α-(meth)acryloyloxy-α,β,β,γ,γ-pentamethyl-γ-butyrolactone.

Examples of the monomeric units having a lactone skeleton [other than the monomeric units represented by Formula (I)] further include monomers each composed of (meth)acrylic acid to which a polycyclic ester group having both an electron-withdrawing substituent and a lactone skeleton is directly bound. The monomeric units are represented by following Formula (V):

[Chemical Formula 16]

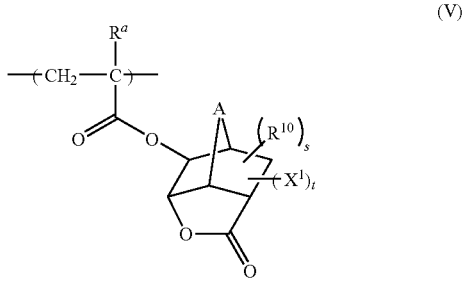

(V)

In Formula (V), $R^a$ is as defined above. $R^{10}$s are substituents bound to the ring and each represent a halogen atom, an alkyl or haloalkyl group having 1 to 6 carbon atoms, a hydroxyalkyl or hydroxyhaloalkyl group having 1 to 6 carbon atoms whose hydroxyl moiety may be protected by a protecting group, a carboxyl group which may form a salt, or a substituted oxycarbonyl group. "A" represents an alkylene group having 1 to 6 carbon atoms, an oxygen atom, a sulfur atom, or nonbonding. The symbol "s" is the number of $R^{10}$s and denotes an integer of 0 to 8. $X^1$s each represent an electron-withdrawing substituent; and the symbol "t" is the number of $X^1$s bound to the ring and denotes an integer of 1 to 9. The —COO— group bound to the polymer chain may have either endo or exo configuration.

Examples of the halogen atom and other groups as $R^{10}$s are as with the examples of the halogen atom and other groups as $R^1$s. Examples of the electron-withdrawing substituent as $X^1$s are as with the examples of the electron-withdrawing substituent as Xs.

Representative examples of monomers corresponding to the monomeric units represented by Formula (IV) include compounds corresponding to the compounds exemplified as representative examples of the monomers represented by Formula (1) having an electron-withdrawing substituent and a lactone skeleton, except for replacing R by a $CH_2=C(R^a)$ CO— group. Specifically, representative examples of such compounds include 1-cyano-5-methacryloyloxy-3-oxatricyclo[4.2.1.0$^{4,8}$]nonan-2-one, 1-cyano-9-methyl-5-methacryloyloxy-3-oxatricyclo[4.2.1.0$^{4,8}$]nonan-2-one, 1-cyano-7,7-dimethyl-5-methacryloyloxy-3-oxatricyclo[4.2.1.0$^{4,8}$]nonan-2-one, 1-cyano-5-methacryloyloxy-3,7-dioxatricyclo[4.2.1.0$^{4,8}$]nonan-2-one, 1-fluoro-5-methacryloyloxy-3-oxatricyclo[4.2.1.0$^{4,8}$]nonan-2-one, 1-fluoro-9-methyl-5-methacryloyloxy-3-oxatricyclo[4.2.1.0$^{4,8}$]nonan-2-one, 1-fluoro-7,7-dimethyl-5-methacryloyloxy-3-oxatricyclo[4.2.1.0$^{4,8}$]nonan-2-one, 1-fluoro-5-methacryloyloxy-3,7-dioxatricyclo[4.2.1.0$^{4,8}$]nonan-2-one, 1-trifluoromethyl-5-methacryloyloxy-3-oxatricyclo[4.2.1.0$^{4,8}$]nonan-2-one, 1-trifluoromethyl-9-methyl-5-methacryloyloxy-3-oxatricyclo[4.2.1.0$^{4,8}$]nonan-2-one, 1-trifluoromethyl-7,7-dimethyl-5-methacryloyloxy-3-oxatricyclo[4.2.1.0$^{4,8}$]nonan-2-one, and 1-trifluoromethyl-5-methacryloyloxy-3,7-dioxatricyclo[4.2.1.0$^{4,8}$]nonan-2-one.

Such a monomer corresponding to the monomeric unit represented by Formula (IV) can be prepared, for example, by reacting the compound represented by Formula (5) with the unsaturated carboxylic acid represented by Formula (7) or a reactive derivative thereof. More specifically, the monomer can be prepared typically by any of processes (a), (b), and (c). In the process (a), the compound represented by Formula (5) is reacted with an active reactive derivative of an unsaturated carboxylic acid in a solvent (e.g., tetrahydrofuran, toluene, or methylene chloride) and, where necessary, in the presence of a base (e.g., triethylamine, pyridine, or 4-dimethylaminopyridine). Exemplary active reactive derivatives of unsaturated carboxylic acids include (meth)acrylyl halides such as (meth)acrylyl chlorides; and (meth)acrylic anhydrides. In the process (b), the compound represented by Formula (5) is reacted with an unsaturated carboxylic ester (e.g., methyl(meth)acrylate) in a solvent as in the process (a) and in the presence of a transesterification catalyst (e.g., titanium isopropoxide). In the process (c), the compound represented by Formula (5) is reacted with an unsaturated carboxylic acid (e.g., (meth)acrylic acid) in a solvent as in the process (a) and in the presence of a strong acid (e.g., hydrochloric acid, sulfuric acid, or p-toluenesulfonic acid). Reaction conditions in these processes are as in regular production processes of esters.

Though not critical, the content of the monomeric units represented by Formula (I) in the polymeric compound according to the present invention is generally about 1 to 90 percent by mole, preferably about 5 to 80 percent by mole, and more preferably about 10 to 60 percent by mole, based on the total amount of monomeric units constituting the polymer (polymeric compound). The content of monomeric units part of which will leave with an acid to allow the polymeric compound to be soluble in an alkali is typically about 10 to 95 percent by mole, preferably about 15 to 90 percent by mole, and more preferably about 20 to 60 percent by mole. The content of monomeric unit(s) corresponding to at least one monomer selected from the group consisting of hydroxyl-containing monomers, mercapto-containing monomers, and carboxyl-containing monomers is typically about 0 to 60 percent by mole, preferably about 5 to 50 percent by mole, and more preferably about 10 to 40 percent by mole. Examples of the monomeric units just mentioned above include monomeric units represented by Formula (III) in which at least one of $qR^9$s is a protected or unprotected hydroxyl group, a protected or unprotected hydroxyalkyl group, a protected or unprotected mercapto group, or a protected or unprotected carboxyl group.

Polymerization of a mixture of monomers for the production of the polymeric compounds according to the present invention can be carried out by a process customarily used in the preparation typically of acrylic polymers. Such processes include solution polymerization, bulk polymerization, suspension polymerization, bulk-suspension polymerization, and emulsion polymerization. Among them, solution polymerization processes are preferred, of which drop polymerization is more preferred. Specifically, the drop polymerization can be performed, for example, by any of the following processes (i), (ii), and (iii). In the process (i), a solution of monomers in an organic solvent, and a solution of a polymerization initiator in the organic solvent are previously prepared respectively, and these solutions are respectively added dropwise to the organic solvent held at a constant temperature. In the process (ii), a mixed solution containing monomers and a polymerization initiator in an organic solvent is prepared and added dropwise to the organic solvent held at a constant temperature. In the process (iii), a solution of monomers in an organic solvent, and a solution of a polymerization initiator in the organic solvent are prepared respectively, and the solution of polymerization initiator is added dropwise to the solution of monomers held at a constant temperature.

The solvent used in the polymerization can be any of known solvents. Examples of such solvents include ethers such as chain ethers (e.g., diethyl ether, and propylene glycol monomethyl ether and other glycol ethers) and cyclic ethers (e.g., tetrahydrofuran and dioxane); esters such as methyl acetate, ethyl acetate, butyl acetate, ethyl lactate, and glycol ether esters (e.g., propylene glycol monomethyl ether acetate); ketones such as acetone, methyl ethyl ketone, methyl isobutyl ketone, and cyclohexanone; amides such as N,N-dimethylacetamide and N,N-dimethylformamide; sulfoxides such as dimethyl sulfoxide; alcohols such as methanol, ethanol, and propanol; hydrocarbons such as aromatic hydrocarbons (e.g., benzene, toluene, and xylenes), aliphatic hydrocarbons (e.g., hexane), and alicyclic hydrocarbons (e.g., cyclohexane); and mixtures of these solvents. The polymerization initiator can be any of known polymerization initiators. The polymerization temperature can be chosen as appropriate within the range typically of about 30° C. to 150° C.

Polymers prepared through polymerization can be purified by precipitation or reprecipitation. A solvent for use in precipitation or reprecipitation may be either an organic solvent or water and may also be a solvent mixture. Exemplary organic solvents for use as the solvent in precipitation or reprecipitation include hydrocarbons including aliphatic hydrocarbons (e.g., pentane, hexane, heptane, and octane), alicyclic hydrocarbons (e.g., cyclohexane and methylcyclohexane), and aromatic hydrocarbons (e.g., benzene, toluene, and xylenes); halogenated hydrocarbons such as halogenated aliphatic hydrocarbons (e.g., methylene chloride, chloroform, and carbon tetrachloride) and halogenated aromatic hydrocarbons (e.g., chlorobenzene and dichlorobenzene); nitro compounds such as nitromethane and nitroethane; nitriles such as acetonitrile and benzonitrile; ethers such as chain ethers (e.g., diethyl ether, diisopropyl ether, and dimethoxyethane) and cyclic ethers (e.g., tetrahydrofuran and dioxane); ketones such as acetone, methyl ethyl ketone, and diisobutyl ketone; esters such as ethyl acetate and butyl acetate; carbonates such as dimethyl carbonate, diethyl carbonate, ethylene carbonate, and propylene carbonate; alcohols such as methanol, ethanol, propanol, isopropyl alcohol, and butanol; carboxylic acids such as acetic acid; and solvent mixtures containing these solvents.

Among them, a solvent mixture containing both methanol and water and solvents containing at least a hydrocarbon are preferred as organic solvents for use in the precipitation or reprecipitation. Aliphatic hydrocarbons such as hexane are preferred as the hydrocarbon. The ratio of the hydrocarbon (e.g., an aliphatic hydrocarbon such as hexane) to another solvent in the solvent containing at least the hydrocarbon is typically about 10/90 to 99/1, preferably about 30/70 to 98/2, and more preferably about 50/50 to 97/3, in terms of volume ratio at 25° C.

The polymeric compounds may each have a weight-average molecular weight (Mw) of typically about 1000 to 500000 and preferably about 3000 to 50000, and a molecular weight distribution (Mw/Mn) of typically about 1.5 to 2.5. The symbol Mn indicates a number-average molecular weight, and Mn and Mw are molecular weights both in terms of polystyrene.

The polymeric compounds according to the present invention are highly stable and resistant typically to chemicals, are excellently soluble in an organic solvent, are highly hydrolyzable, and hydrolyzed products thereof are satisfactorily soluble in water. Accordingly, they can be used as highly functional polymers in various fields.

Photoresist compositions according to the present invention each contain at least the polymeric compound according to the present invention and a light-activatable acid generator and generally further contain a resist solvent. The photoresist compositions can be prepared, for example, by adding a light-activatable acid generator to a solution (solution in a resist solvent) of the polymeric compound according to the present invention.

Exemplary light-activatable acid generators include common or known compounds that efficiently generate an acid upon the irradiation with light (exposure), including diazonium salts; iodonium salts such as diphenyliodo hexafluorophosphate; sulfonium salts such as triphenylsulfonium hexafluoroantimonate, triphenylsulfonium hexafluorophosphate, and triphenylsulfonium methanesulfonate; sulfonic acid esters such as 1-phenyl-1-(4-methylphenyl)sulfonyloxy-1-benzoylmethane, 1,2,3-trisulfonyloxymethylbenzene, 1,3-dinitro-2-(4-phenylsulfonyloxymethyl)benzene, and 1-phenyl-1-(4-methylphenylsulfonyloxymethyl)-1-hydroxy-1-benzoylmethane; oxathiazole derivatives; s-triazine derivatives; disulfone derivatives such as diphenyldisulfone; imide compounds; oxime sulfonates; diazonaphthoquinones; and benzoin tosylates. Each of these light-activatable acid generators can be used alone or in combination.

The amount of light-activatable acid generators can be chosen as appropriate according typically to the strength of an acid generated upon the irradiation with light and the contents of respective constitutional repeating units in the polymer (photoresist resin). Typically, the amount can be chosen within the ranges of typically about 0.1 to 30 parts by weight, preferably about 1 to 25 parts by weight, and more preferably about 2 to 20 parts by weight, per 100 parts by weight of the polymer.

Exemplary resist solvents include the glycol solvents, ester solvents, and ketone solvents exemplified as the polymerization solvent, and mixtures of these solvents. Among them, propylene glycol monomethyl ether, propylene glycol monomethyl ether acetate, ethyl lactate, methyl isobutyl ketone, methyl amyl ketone, and mixtures of these are preferred, of which more preferred are solvents containing at least propylene glycol monomethyl ether acetate, such as propylene glycol monomethyl ether acetate alone; a solvent mixture containing both propylene glycol monomethyl ether acetate and propylene glycol monomethyl ether; and a solvent mixture containing both propylene glycol monomethyl ether acetate and ethyl lactate.

The concentration of the polymer in the photoresist composition is typically about 10 to 40 percent by weight. The photoresist composition may further contain one or more other components including alkali-soluble components such as alkali-soluble resins (e.g., novolak resins, phenol resins, imide resins, and carboxyl-containing resins); and colorants (e.g., dyestuffs).

The resulting photoresist composition is usable for highly accurate fine patterning (formation of a fine pattern), by applying the photoresist composition to a base or substrate, drying the applied film, applying light through a predetermined mask to the coat film (resist film) (or further performing post-exposure bake) to form a latent image pattern, and subsequently developing the latent image pattern.

Exemplary bases or substrates include silicon wafers, metals, plastics, glass, and ceramics. The application of the photoresist composition can be performed using a common coating device such as spin coater, dip coater, or roller coater. The thickness of the coat film is typically about 0.1 to 20 μm and preferably about 0.3 to 2 μm.

The light application (exposure) can be performed using rays with various wavelengths, such as ultraviolet rays and X-rays. For semiconductor resists, g-ray, i-ray, and excimer laser beams (e.g., XeCl, KrF, KrCl, ArF, or ArCl laser) are used. The exposure energy is typically about 1 to 1000 mJ/cm$^2$ and preferably about 10 to 500 mJ/cm$^2$.

The light application allows the light-activatable acid generator to generate an acid, and this acid acts on a protecting group (leaving group) typically of carboxyl group of the constitutional repeating unit part of which will leave with an acid to allow the polymeric compound to be soluble in an alkali (constitutional repeating unit having an acid-leaving group) typically of the photoresist polymeric compound to leave immediately to form a group, such as carboxyl group, that helps the polymeric compound to be soluble. Thus, the subsequent development with water or an alkaline developer gives a predetermined pattern with a high accuracy.

EXAMPLES

The present invention will be illustrated in further detail with reference to several working examples below. It should be noted, however, that these examples are never construed to limit the scope of the present invention. The symbol "Et" in chemical formulae below represents an ethyl group. The weight-average molecular weight (Mw) and the number-average molecular weight (Mn) of a sample polymer are values in terms of standard polystyrene as determined through gel permeation chromatography (GPC) using a refractive index detector (RI) and tetrahydrofuran solvent. The gel permeation chromatography was carried out using three columns "KF-806L" (supplied by Showa Denko K.K.) connected in series under conditions of a column temperature of 40° C., an RI temperature of 40° C., and a tetrahydrofuran flow rate of 0.8 ml/min.

Production Example 1

According to the following reaction scheme, 1-cyano-5-hydroxy-3-oxatricyclo[4.2.1.0$^{4,8}$]nonan-2-one was prepared.

[Chemical Formula 17]

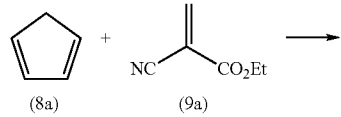

-continued

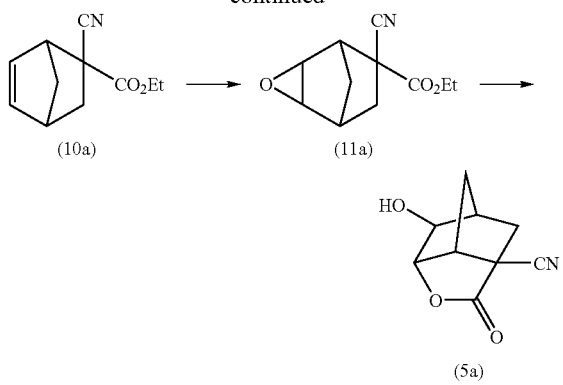

In 200 ml of toluene, was dissolved 50 g (0.33 mol) of 2-cyanoethyl acrylate (9a) to give a solution, and 45 g (0.68 mol) of 1,3-cyclopentadiene (8a) was added dropwise to the solution with cooling at a temperature of 35° C. or lower. After stirring for 1 hour, the mixture was concentrated and thereby yielded 72 g of ethyl 5-cyanobicyclo[2.2.1]hept-2-ene-5-carboxylate represented by Formula (10a) (crude product).

The above-prepared compound (crude product) represented by Formula (10a) (69 g; in terms of 0.36 mol) was dissolved in 501 g of methylene chloride to give a solution, and 115 g of m-CPBA (m-chloroperbenzoic acid) was gradually added to the solution with cooling at 5° C. or lower. After 4 hours, an aqueous sodium sulfite solution was added to decompose excess peroxide, and the organic layer was washed with an aqueous sodium hydrogen carbonate solution. The organic layer [containing a compound represented by Formula (11a)] was combined with 150 g of formic acid and 303 g of water and heated to 50° C., followed by continuous stirring for 4 hours. Extraction with ethyl acetate was performed until an aqueous layer contained no product. The combined organic layers were concentrated and thereby yielded 23 g of 1-cyano-5-hydroxy-3-oxatricyclo[4.2.1.0$^{4,8}$]nonan-2-one represented by Formula (5a) (crude product).

[Spectral data of 1-cyano-5-hydroxy-3-oxatricyclo[4.2.1.0$^{4,8}$]nonan-2-one represented by Formula (5a)]

$^1$H-NMR (CDCl$_3$) δ: 4.52-4.54 (1H), 3.69-3.73 (2H), 2.54-2.55 (1H), 2.29-2.35 (2H), 2.13-2.16 (1H), 1.85-1.88 (1H)

Example 1

According to the following reaction scheme, 1-cyano-5-(2-methacryloyloxyacetoxy)-3-oxatricyclo[4.2.1.0$^{4,8}$]nonan-2-one was prepared.

[Chemical Formula 18]

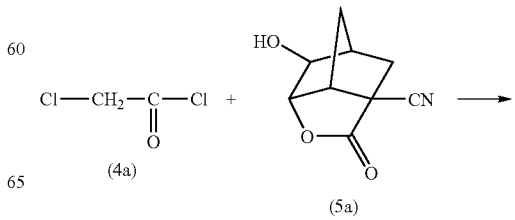

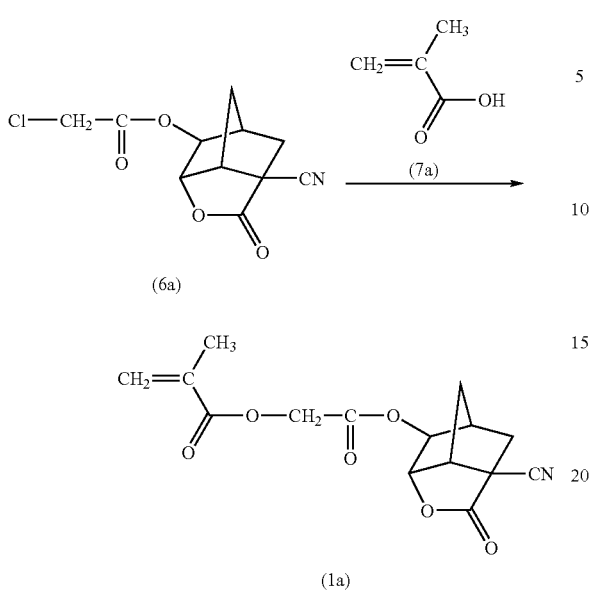

In a nitrogen-purged 500-ml three-neck flask equipped with a stirrer, were placed 10 g (56 mmol) of 1-cyano-5-hydroxy-3-oxatricyclo[4.2.1.0$^{4,8}$]nonan-2-one represented by Formula (5a), 20 g of acetonitrile, and 28.0 g (184 mmol) of 1,8-diazabicyclo[5.4.0]undec-7-ene, followed by stirring to give a solution. To the solution on an ice bath, 18.9 g (167 mmol) of 2-chloroacetyl chloride represented by Formula (4a) was added dropwise over 2 hours while maintaining the internal temperature at 3° C. to 10° C. After dropwise addition, the mixture was warmed to 40° C. and stirred for 5 hours while maintaining that temperature (40° C.). The reaction mixture was combined with 200 g of ethyl acetate and further combined with 20 g of water gradually added, while maintaining the internal temperature at 2° C. to 15° C. The organic layer was separated, washed sequentially with three portions of 30 g of a 8 percent by weight aqueous sodium hydrogen carbonate solution, two portions of 30 g of 2N hydrochloric acid, and three portions of 30 g of water, concentrated under reduced pressure, and thereby yielded 9.8 g (38 mmol; in a yield of 68%) of 1-cyano-5-(2-chloroacetoxy)-3-oxatricyclo[4.2.1.0$^{4,8}$]nonan-2-one represented by Formula (6a). NMR data of this compound is shown below.

$^1$H-NMR (DMSO-d6) δ: 4.79 (1H, m), 4.66 (1H, m), 4.32-4.43 (2H, m), 3.79 (1H, m), 2.59 (1H, m), 2.28-2.39 (2H, m), 2.00 (1H, m), 1.85 (1H, m)

In a nitrogen-purged 500-ml three-neck flask equipped with a stirrer, were placed 1.95 g (14.1 mmol) of potassium carbonate, 0.18 g (1.2 mmol) of sodium iodide, 3.0 mg of phenothiazine, 6.0 g of N,N-dimethylformamide, and 3.0 g (11.7 mmol) of the above-prepared 1-cyano-5-(2-chloroacetoxy)-3-oxatricyclo[4.2.1.0$^{4,8}$]nonan-2-one; and 1.21 g (14.1 mmol) of methacrylic acid was added dropwise to the stirred mixture over 15 minutes while maintaining the internal temperature at 30° C. to 40° C. on a warm water bath. After the dropwise addition, the mixture was further stirred for 5 hours while maintaining its temperature at 35° C. The reaction mixture was combined with 36 g of ethyl acetate and further combined with 27 g of water gradually added while maintaining the internal temperature at 20° C. The organic layer was separated, washed sequentially with two portions of 9.0 g of a 8 percent by weight aqueous sodium hydrogen carbonate solution and three portions of 9.0 g of water, and concentrated under reduced pressure. The resulting concentrate was purified through silica-gel chromatography with a mixture of hexane and ethyl acetate as an eluent and thereby yielded 1.4 g (4.6 mmol, in a yield of 39%) of 1-cyano-5-(2-methacryloyloxyacetoxy)-3-oxatricyclo[4.2.1.0$^{4,8}$]nonan-2-one represented by Formula (1a). NMR data of this compound is shown below.

$^1$H-NMR (CDCl$_3$) δ: 6.21 (1H, m), 5.70 (1H, m), 4.64-4.72 (4H, m), 3.65 (1H, m), 2.74 (1H, m), 2.39 (1H, dd), 2.26 (1H, dd), 2.12-2.19 (1H, m), 1.94-2.00 (4H, m)

Example 2

Synthesis of Polymeric Compound of Following Structure

[Chemical Formula 19]

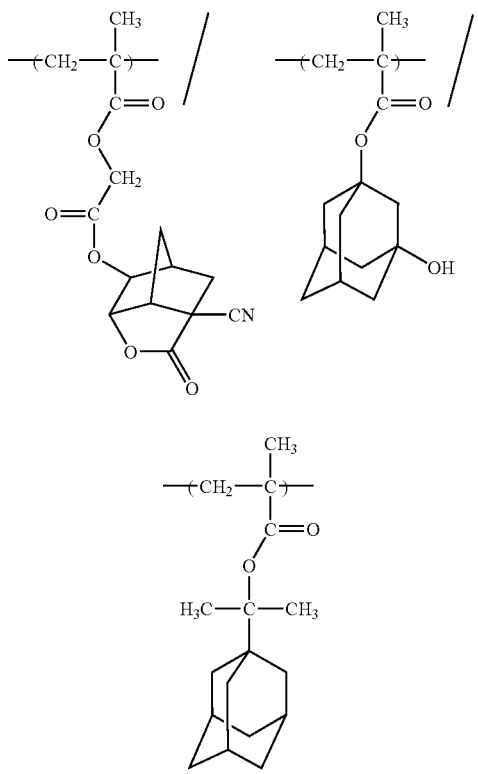

In a nitrogen atmosphere, 35.7 g of propylene glycol monomethyl ether acetate (PGMEA) and 23.8 g of propylene glycol monomethyl ether (PGME) were placed in a round-bottomed flask equipped with a reflux condenser, a stirring bar, and a three-way stopcock to give a mixture; and a monomer solution was added dropwise at a constant rate over 6 hours to the mixture while stirring the mixture and maintaining the temperature at 80° C. The monomer solution was a mixture of 13.36 g (43.8 mmol) of 1-cyano-5-(2-methacryloyloxyacetoxy)-3-oxatricyclo[4.2.1.0$^{4,8}$]nonan-2-one, 5.17 g (21.9 mmol) of 1-hydroxy-3-methacryloyloxyadamantane, 11.47 g (43.8 mmol) of 1-(1-methacryloyloxy-1-methylethyl)adamantane, 1.80 g of dimethyl 2,2'-azobisisobutylate [supplied by Wako Pure Chemical Industries Ltd. under the trade name "V-601"], 66.3 g of PGMEA, and 44.2 g of PGME. After the completion of dropwise addition, the mixture was further stirred for 2 hours. After the completion of polymerization reaction, the reaction mixture (solution) was added dropwise to a 9:1 (volume ratio; 25° C.) mixture of hexane and ethyl acetate in an amount of 7 times that of the reaction mixture while stirring the mixture, to give precipitates. The precipitates were collected by filtration, dried under reduced pressure, and thereby yielded 26.8 g of the target resin (polymer). The recovered polymer was analyzed through GPC and was found to have a weight-average molecular weight (Mw) of 8200 and a molecular weight distribution (Mw/Mn) of 1.87.

Example 3

Synthesis of Polymeric Compound of Following Structure

[Chemical Formula 20]

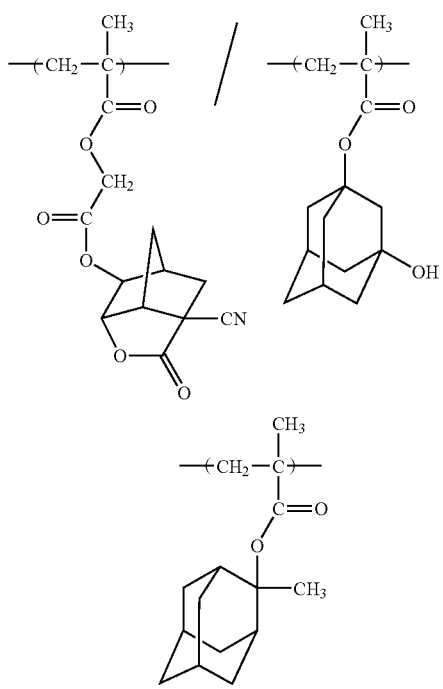

The procedure of Example 2 was performed, except for using, 13.93 g (45.7 mmol) of 1-cyano-5-(2-methacryloyloxyacetoxy)-3-oxatricyclo[4.2.1.0$^{4,8}$]nonan-2-one, 5.39 g (22.8 mmol) of 1-hydroxy-3-methacryloyloxyadamantane, and 10.68 g (45.7 mmol) of 2-methacryloyloxy-2-methyladamantane instead of the monomer components used in Example 2, and thereby yielded 26.2 g of the target resin (polymer). The recovered polymer was analyzed through GPC and was found to have a weight-average molecular weight (Mw) of 8700 and a molecular weight distribution (Mw/Mn) of 1.90.

Example 4

Synthesis of Polymeric Compound of Following Structure

[Chemical Formula 21]

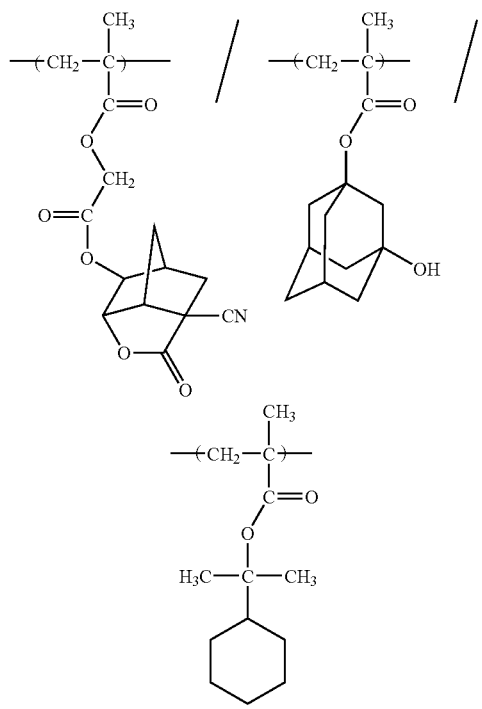

The procedure of Example 2 was performed, except for using 14.45 g (47.4 mmol) of 1-cyano-5-(2-methacryloyloxyacetoxy)-3-oxatricyclo[4.2.1.0$^{4,8}$]nonan-2-one, 5.59 g (23.7 mmol) of 1-hydroxy-3-methacryloyloxyadamantane, and 9.95 g (47.4 mmol) of 1-(1-methacryloyloxy-1-methylethyl)cyclohexane instead of the monomer components used in Example 2, and thereby yielded 25.6 g of the target resin (polymer). The recovered polymer was analyzed through GPC and was found to have a weight-average molecular weight (Mw) of 9100 and a molecular weight distribution (Mw/Mn) of 1.85.

Example 5

Synthesis of Polymeric Compound of Following Structure

[Chemical Formula 22]

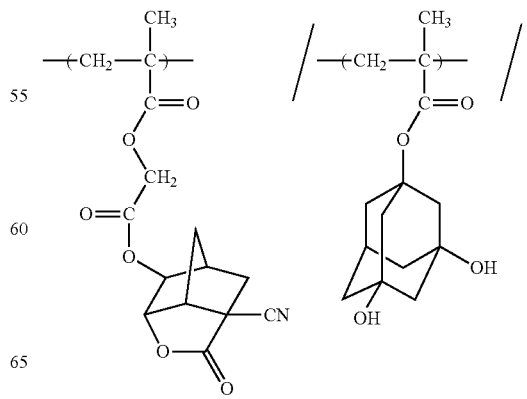

-continued

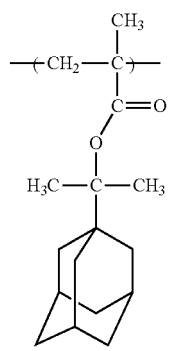

The procedure of Example 2 was performed, except for using 13.20 g (43.3 mmol) of 1-cyano-5-(2-methacryloyloxyacetoxy)-3-oxatricyclo[4.2.1.0⁴,⁸]nonan-2-one, 5.45 g (21.6 mmol) of 1,3-dihydroxy-5-methacryloyloxyadamantane, and 11.34 g (43.3 mmol) of 1-(1-methacryloyloxy-1-methylethyl)adamantane instead of the monomer components used in Example 2, and thereby yielded 26.7 g of the target resin (polymer). The recovered polymer was analyzed through GPC and was found to have a weight-average molecular weight (Mw) of 8300 and a molecular weight distribution (Mw/Mn) of 1.87.

Example 6

Synthesis of Polymeric Compound of Following Structure

[Chemical Formula 23]

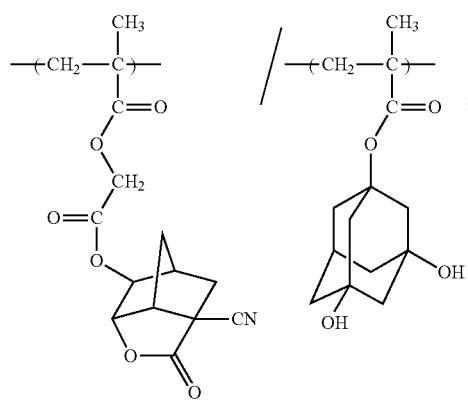

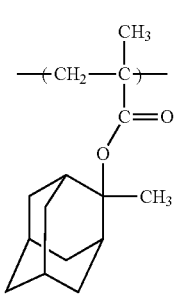

The procedure of Example 2 was performed, except for using 13.76 g (45.1 mmol) of 1-cyano-5-(2-methacryloyloxyacetoxy)-3-oxatricyclo[4.2.1.0⁴,⁸]nonan-2-one, 5.68 g (22.6 mmol) of 1,3-dihydroxy-5-methacryloyloxyadamantane, and 10.56 g (45.1 mmol) of 2-methyl-2-methacryloyloxyadamantane instead of the monomer components used in Example 2, and thereby yielded 26.5 g of the target resin (polymer). The recovered polymer was analyzed through GPC and was found to have a weight-average molecular weight (Mw) of 8500 and a molecular weight distribution (Mw/Mn) of 1.89.

Example 7

Synthesis of Polymeric Compound of Following Structure

[Chemical Formula 24]

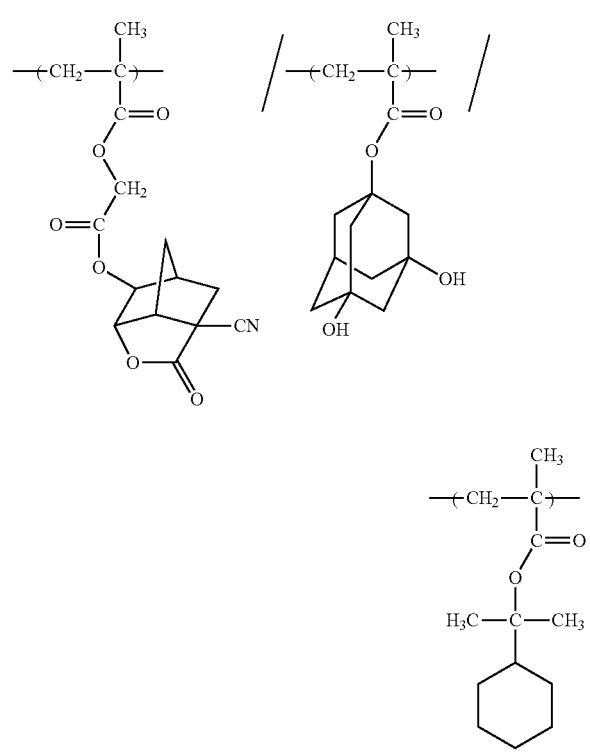

The procedure of Example 2 was performed, except for using 14.27 g (46.8 mmol) of 1-cyano-5-(2-methacryloyloxyacetoxy)-3-oxatricyclo[4.2.1.0⁴,⁸]nonan-2-one, 5.90 g (23.4 mmol) of 1,3-dihydroxy-5-methacryloyloxyadamantane, and 9.83 g (46.8 mmol) of 1-(1-methacryloyloxy-1-methylethyl)cyclohexane instead of the monomer components used in Example 2, and thereby yielded 25.4 g of the target resin (polymer). The recovered polymer was analyzed through GPC and was found to have a weight-average molecular weight (Mw) of 9000 and a molecular weight distribution (Mw/Mn) of 1.88.

Comparative Example 1

Synthesis of Polymeric Compound of Following Structure

[Chemical Formula 25]

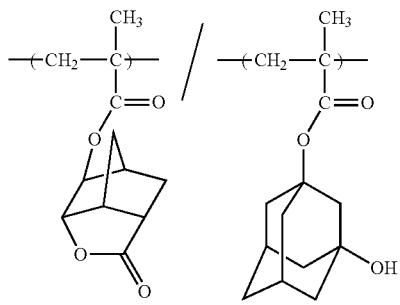
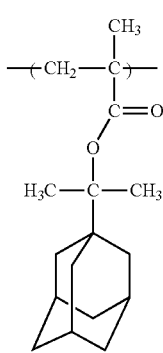

The procedure of Example 2 was performed, except for using 11.06 g (49.8 mmol) of 5-methacryloyloxy-3-oxatricyclo[4.2.1.0$^{4,8}$]nonan-2-one instead of 13.36 g (43.8 mmol) of 1-cyano-5-(2-methacryloyloxyacetoxy)-3-oxatricyclo [4.2.1.0$^{4,8}$]nonan-2-one used in Example 2, and thereby yielded 26.6 g of the target resin (polymer). The recovered polymer was analyzed through GPC and was found to have a weight-average molecular weight (Mw) of 9100 and a molecular weight distribution (Mw/Mn) of 1.89.

Comparative Example 2

Synthesis of Polymeric Compound of Following Structure

[Compound Formula 26]

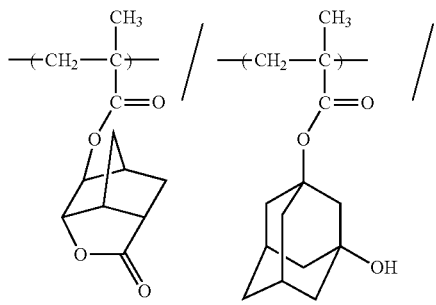
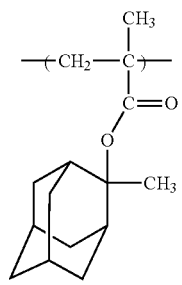

The procedure of Example 3 was performed, except for using 11.60 g (52.3 mmol) of 5-methacryloyloxy-3-oxatricyclo[4.2.1.0$^{4,8}$]nonan-2-one instead of 13.93 g (45.7 mmol) of 1-cyano-5-(2-methacryloyloxyacetoxy)-3-oxatricyclo [4.2.1.0$^{4,8}$]nonan-2-one used in Example 3, and thereby yielded 26.3 g of the target resin (polymer). The recovered polymer was analyzed through GPC and was found to have a weight-average molecular weight (Mw) of 9700 and a molecular weight distribution (Mw/Mn) of 1.87.

Comparative Example 3

Synthesis of Polymeric Compound of Following Structure

[Compound Formula 27]

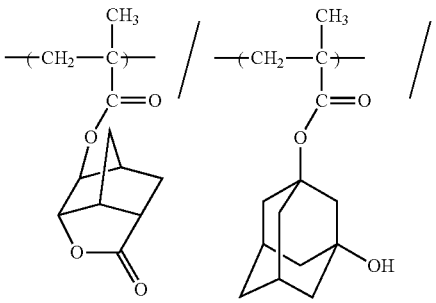
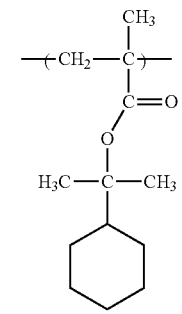

The procedure of Example 4 was performed, except for using 12.11 g (54.5 mmol) of 5-methacryloyloxy-3-oxatricyclo[4.2.1.0$^{4,8}$]nonan-2-one instead of 14.45 g (47.4 mmol) of 1-cyano-5-(2-methacryloyloxyacetoxy)-3-oxatricyclo [4.2.1.0$^{4,8}$]nonan-2-one used in Example 4, and thereby yielded 25.1 g of the target resin (polymer). The recovered polymer was analyzed through GPC and was found to have a weight-average molecular weight (Mw) of 10000 and a molecular weight distribution (Mw/Mn) of 1.90.

Comparative Example 4

Synthesis of Polymeric Compound of Following Structure

[Compound Formula 28]

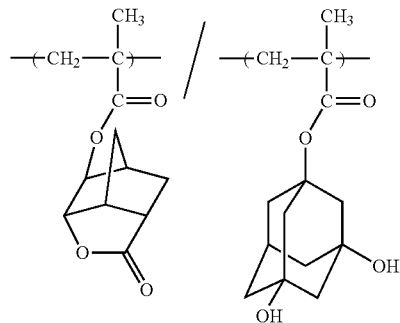

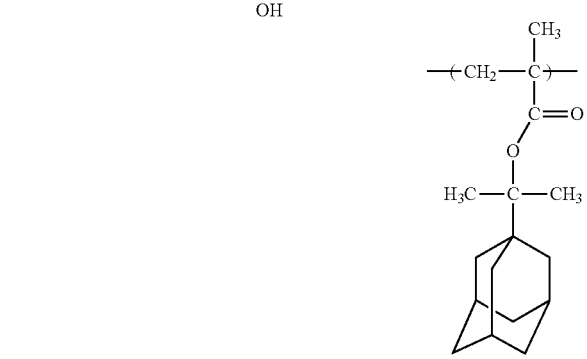

The procedure of Example 5 was performed, except for using 10.92 g (49.2 mmol) of 5-methacryloyloxy-3-oxatricyclo[4.2.1.0$^{4,8}$]nonan-2-one instead of 13.20 g (43.3 mmol) of 1-cyano-5-(2-methacryloyloxyacetoxy)-3-oxatricyclo [4.2.1.0$^{4,8}$]nonan-2-one used in Example 5, and thereby yielded 27.0 g of the target resin (polymer). The recovered polymer was analyzed through GPC and was found to have a weight-average molecular weight (Mw) of 9000 and a molecular weight distribution (Mw/Mn) of 1.93.

Comparative Example 5

Synthesis of Polymeric Compound of Following Structure

[Compound Formula 29]

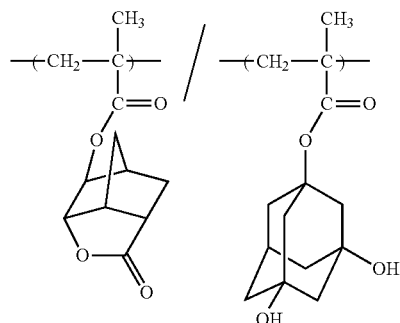

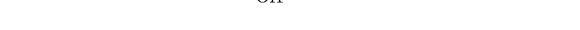

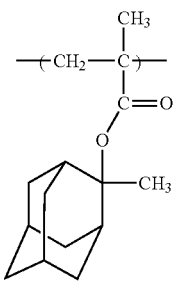

The procedure of Example 6 was performed, except for using 11.44 g (51.5 mmol) of 5-methacryloyloxy-3-oxatricyclo[4.2.1.0$^{4,8}$]nonan-2-one instead of 13.76 g (45.1 mmol) of 1-cyano-5-(2-methacryloyloxyacetoxy)-3-oxatricyclo [4.2.1.0$^{4,8}$]nonan-2-one used in Example 6, and thereby yielded 27.1 g of the target resin (polymer). The recovered polymer was analyzed through GPC and was found to have a weight-average molecular weight (Mw) of 8700 and a molecular weight distribution (Mw/Mn) of 1.92.

Comparative Example 6

Synthesis of Polymeric Compound of Following Structure

[Compound Formula 30]

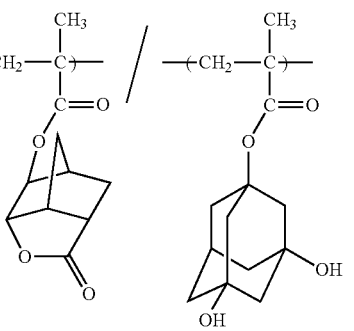

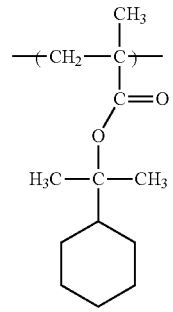

The procedure of Example 7 was performed, except for using 11.94 g (53.8 mmol) of 5-methacryloyloxy-3-oxatricyclo[4.2.1.0$^{4,8}$]nonan-2-one instead of 14.27 g (46.8 mmol) of 1-cyano-5-(2-methacryloyloxyacetoxy)-3-oxatricyclo [4.2.1.0$^{4,8}$]nonan-2-one used in Example 7, and thereby yielded 25.8 g of the target resin (polymer). The recovered polymer was analyzed through GPC and was found to have a weight-average molecular weight (Mw) of 9500 and a molecular weight distribution (Mw/Mn) of 1.88.

Production Example 8

According to the following reaction scheme, 2 (methacryloyloxy)ethyl 1-cyano-2-oxo-3-oxatricyclo[4.2.1.0⁴,⁸]non-5-yl succinate was prepared.

[Chemical Formula 31]

Example 9

Synthesis of Polymeric Compound of Following Structure

[Compound Formula 32]

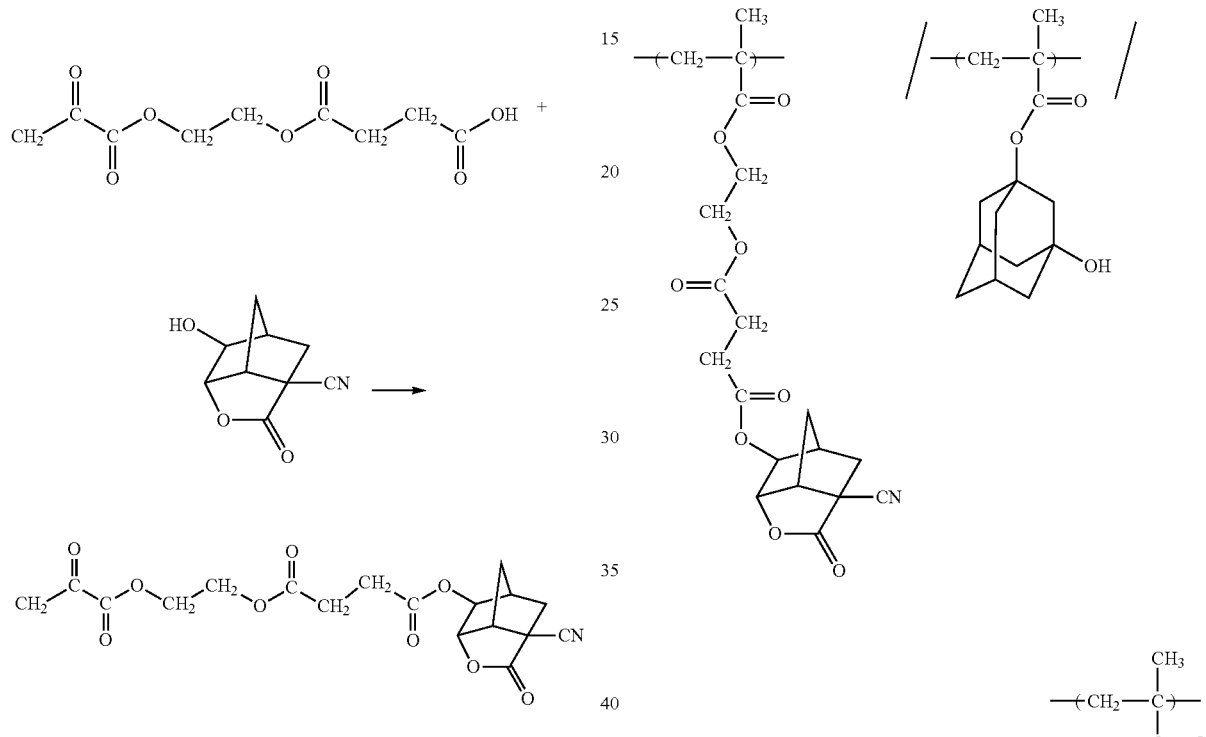

In a nitrogen-purged 500-ml three-neck flask equipped with a stirrer was placed 46.0 g (0.20 mol) of 2-methacryloyloxyethyl hydrogen succinate and acetonitrile. After cooling to 5° C., the mixture was combined with 2.44 g (0.02 mol) of 4-dimethylaminopyridine, 39.3 g (0.205 mol) of 1-ethyl-3-(3-(dimethylaminopropyl)carbodiimide hydrochloride, and 17.9 g (0.10 mol) of 1-cyano-5-hydroxy-3-oxatricyclo[4.2.1.0⁴,⁸]nonan-2-one, followed by a reaction at a liquid temperature of 25° C. for 7 hours. The reaction mixture was combined with 300 cc of ethyl acetate and then washed sequentially with four portions of 300 ml of a 10% aqueous sodium carbonate solution, two portions of 300 ml of 2N hydrochloric acid, and two portions of 300 ml of a 10% brine (aqueous sodium chloride solution), followed by concentration under reduced pressure. The concentrated residue was purified through silica gel column chromatography and thereby yielded 28.2 g (0.072 mol, in a yield of 72%) of 2-(methacryloyloxy)ethyl 1-cyano-2-oxo-3-oxatricyclo[4.2.1.0⁴,⁸]non-5-yl succinate. The NMR data of this compound is shown below.

¹H-NMR (CDCl₃) δ: 6.12 (s, 1H), 5.61 (s, 1H), 4.67 (m, 1H), 4.61 (s, 1H), 4.35 (s, 1H), 3.61 (m, 1H), 2.71 (m, 1H), 2.60-2.69 (m, 4H), 2.36-2.40 (m, 1H), 2.19-2.25 (m, 2H), 1.97 (m, 1H), 1.94 (s, 3H)

The procedure of Example 2 was performed, except for using 15.21 g (38.9 mmol) of 2-(methacryloyloxy)ethyl 1-cyano-2-oxo-3-oxatricyclo[4.2.1.0⁴,⁸]non-5-yl succinate, 4.59 g (19.4 mmol) of 1-hydroxy-3-methacryloyloxyadamantane, and 10.20 g (38.9 mmol) of 1-(1-methacryloyloxy-1-methylethyl)adamantane instead of the monomer components used in Example 2, and thereby yielded 26.5 g of the target resin (polymer). The recovered polymer was analyzed through GPC and was found to have a weight-average molecular weight (Mw) of 9400 and a molecular weight distribution (Mw/Mn) of 1.90.

Example 10

Synthesis of Polymeric Compound of Following Structure

[Chemical Formula 33]

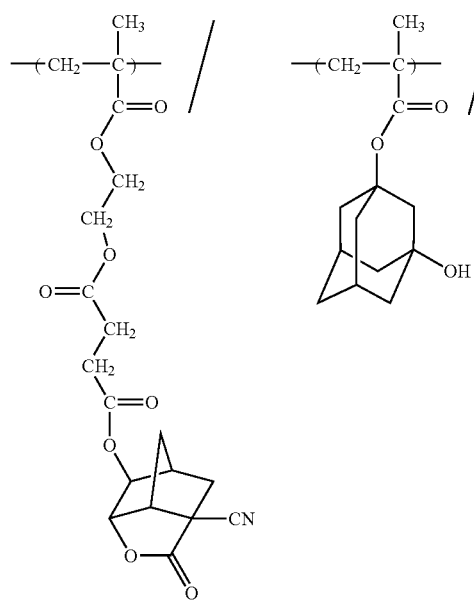

The procedure of Example 2 was performed, except for using 15.79 g (40.3 mmol) of 2-(methacryloyloxy)ethyl 1-cyano-2-oxo-3-oxatricyclo[4.2.1.0$^{4,8}$]non-5-yl succinate, 4.77 g (20.2 mmol) of 1-hydroxy-3-methacryloyloxyadamantane, and 9.45 g (40.3 mmol) of 2-methacryloyloxy-2-methyladamantane instead of the monomer components used in Example 2, and thereby yielded 26.5 g of the target resin (polymer). The recovered polymer was analyzed through GPC and was found to have a weight-average molecular weight (Mw) of 9700 and a molecular weight distribution (Mw/Mn) of 1.93.

Example 11

Synthesis of Polymeric Compound of Following Structure

[Chemical Formula 34]

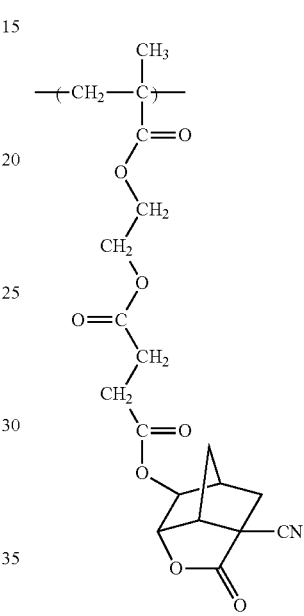

The procedure of Example 2 was performed, except for using 16.31 g (41.7 mmol) of 2-(methacryloyloxy)ethyl 1-cyano-2-oxo-3-oxatricyclo[4.2.1.0$^{4,8}$]non-5-yl succinate, 4.92 g (20.8 mmol) of 1-hydroxy-3-methacryloyloxyadamantane, and 8.77 g (41.7 mmol) of 1-(1-methacryloyloxy-1-methylethyl)cyclohexane instead of the monomer components used in Example 2, and thereby yielded 28.0 g of the target resin (polymer). The recovered polymer was analyzed through GPC and was found to have a weight-average molecular weight (Mw) of 9600 and a molecular weight distribution (Mw/Mn) of 1.95.

Example 12

Synthesis of Polymeric Compound of Following Structure

[Chemical Formula 35]

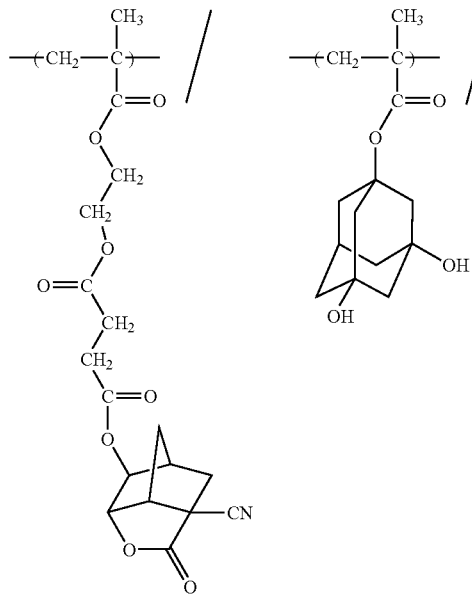

The procedure of Example 2 was performed, except for using 18.70 g (46.2 mmol) of 2-(methacryloyloxy)ethyl 1-cyano-2-oxo-3-oxatricyclo[4.2.1.0$^{4,8}$]non-5-yl succinate, 4.66 g (18.5 mmol) of 1,3-dihydroxy-5-methacryloyloxyadamantane, and 7.27 g (27.7 mmol) of 1-(1-methacryloyloxy-1-methylethyl)adamantane instead of the monomer components used in Example 2, and thereby yielded 26.0 g of the target resin (polymer). The recovered polymer was analyzed through GPC and was found to have a weight-average molecular weight (Mw) of 9000 and a molecular weight distribution (Mw/Mn) of 1.94.

Example 13

Synthesis of Polymeric Compound of Following Structure

[Chemical Formula 36]

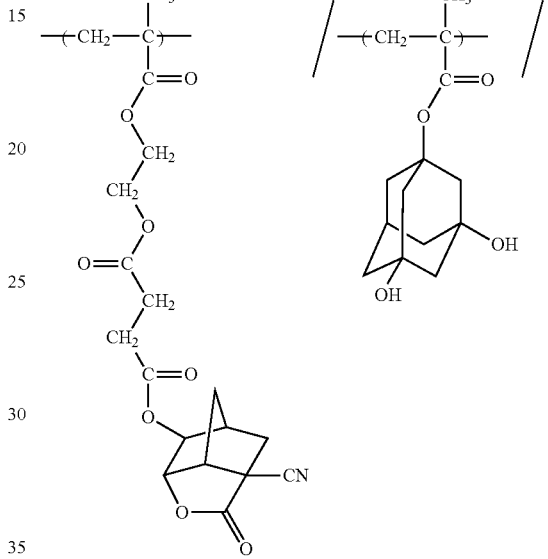

The procedure of Example 2 was performed, except for using 18.55 g (47.4 mmol) of 2-(methacryloyloxy)ethyl 1-cyano-2-oxo-3-oxatricyclo[4.2.1.0$^{4,8}$]non-5-yl succinate, 4.78 g (19.0 mmol) of 1,3-dihydroxy-5-methacryloyloxyadamantane, 6.66 g (28.4 mmol) of 2-methacryloyloxy-2-methyladamantane instead of the monomer components used in Example 2, and thereby yielded 26.0 g of the target resin (polymer). The recovered polymer was analyzed through GPC and was found to have a weight-average molecular weight (Mw) of 9800 and a molecular weight distribution (Mw/Mn) of 1.98.

Example 14

Synthesis of Polymeric Compound of Following Structure

[Chemical Formula 37]

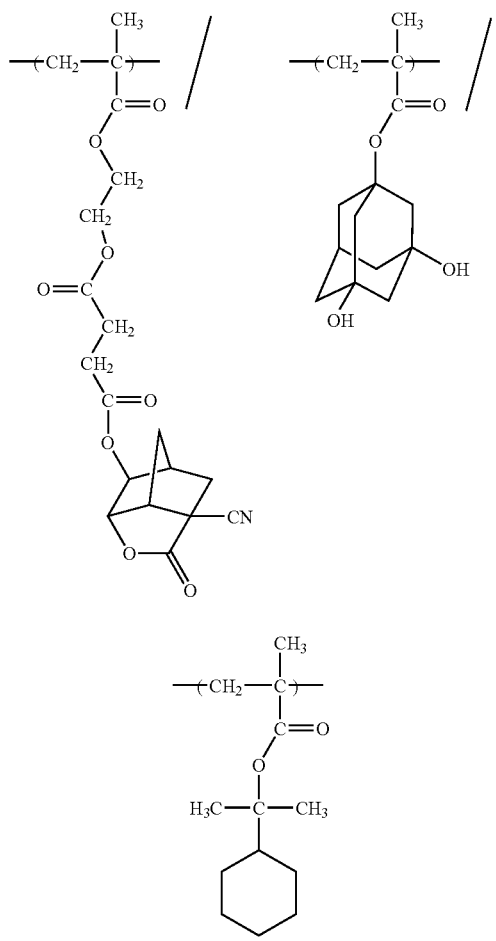

The procedure of Example 2 was performed, except for using 18.98 g (48.4 mmol) of 2-(methacryloyloxy)ethyl 1-cyano-2-oxo-3-oxatricyclo[4.2.1.0$^{4,8}$]non-5-yl succinate, 4.90 g (19.4 mmol) of 1,3-dihydroxy-5-methacryloyloxyadamantane, and 6.12 g (29.1 mmol) of 1-(1-methacryloyloxy-1-methylethyl)cyclohexane instead of the monomer components used in Example 2, and thereby yielded 27.5 g of the target resin (polymer). The recovered polymer was analyzed through GPC and was found to have a weight-average molecular weight (Mw) of 8900 and a molecular weight distribution (Mw/Mn) of 1.87.

Evaluation Tests

Each of the photoresist polymer resins prepared according to the examples and comparative examples was combined with and dissolved in propylene glycol monomethyl ether acetate (PGMEA) and propylene glycol monomethyl ether (PGME) so as to give a solution having a polymer concentration of 20 percent by weight in a 6:4 (by weight) mixture of PGMEA and PGME. The polymer resins according to Examples 2 to 7 were immediately dissolved, whereas the polymer resins according to Comparative Examples 1 to 6 required durations 2 to 4 times longer than those for the examples to be dissolved in the solvent mixture. Each of the resulting photoresist polymer solutions was combined with 10 parts by weight of triphenylsulfonium hexafluoroantimonate per 100 parts by weight of the polymer, further combined with PGMEA to give a polymer concentration of 15 percent by weight, filtrated through a filter with a pore size of 0.02 µm, and thereby yielded a series of photoresist compositions. The polymer solutions according to Examples 2 to 7 and 9 to 14 showed good filterability and could be immediately filtered through the filter with a pore size of 0.02 µm, whereas the polymer solutions according to Comparative Examples 1 to 6 required durations about 5 times longer than those for the polymer solutions according to the examples to be filtered through the filter. The filtration speed of the polymer solutions according to the comparative examples became lower particularly in the latter half of the filtration, anticipating frequent filter exchange.

Each of the resulting photoresist compositions was applied to a silicon wafer by spin coating to give a photosensitive layer 0.7 µm thick. The photosensitive layer was prebaked on a hot plate at a temperature of 100° C. for 150 seconds, exposed to light from ArF excimer laser having a wavelength 193 nm through a mask at an irradiance of 30 mJ/cm$^2$, followed by post-baking at a temperature of 100° C. for 60 seconds. Next, the layer was developed with a 2.38 M aqueous tetramethylammonium hydroxide solution for 60 seconds and rinsed with ultrapure water. The photoresist polymer solutions according to both the examples and comparative examples gave 0.25-µm line-and-space patterns, but the line-and-space patterns according to Examples 2 to 7 and 9 to 14 were obviously clearer than those according to the comparative examples.

The invention claimed is:

1. A polymeric compound comprising at least a monomeric unit represented by following Formula (I):

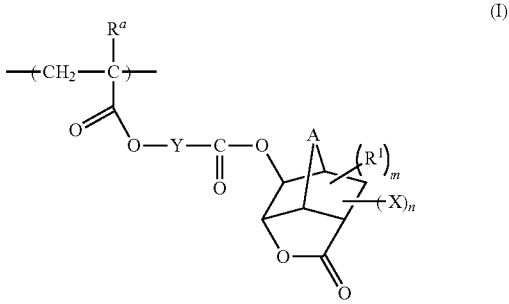

(I)

wherein
$R^a$ represents a hydrogen atom, a halogen atom, or a substituted or unsubstituted alkyl group having 1 to 6 carbon atoms;
$R^1$s are substituents bound to the ring and each represent a halogen atom, an alkyl or haloalkyl group having 1 to 6 carbon atoms, a hydroxyalkyl or hydroxyhaloalkyl group having 1 to 6 carbon atoms whose hydroxyl moiety may be protected by a protecting group, a carboxyl group which may form a salt, or a substituted oxycarbonyl group;

"A" represents an alkylene group having 1 to 6 carbon atoms, an oxygen atom, a sulfur atom, or nonbonding;

"m" is the number of $R^1$s and denotes an integer of 0 to 8;

Xs each independently represent an electron-withdrawing substituent selected from the group consisting of: fluorine-containing group, acyloxy group, cyano group, nitro group, sulfo group, alkanesulfonyl group, alkanesulfinyl group and alkoxysulfonyl group, and wherein at least one X is bound directly to the alpha position of the carbonyl group of the lactone ring;

"n" is the number of Xs bound to the ring and denotes an integer of 1 to 9; and

Y represents a methylene or a group composed of an alkylene group having 1 to 3 carbon atoms and an alkylene group having 1 or 2 carbon atoms bound with each other through an ester bond, wherein the —COO—Y—COO— group bound to the polymer chain may have either endo or exo configuration.

2. The polymeric compound according to claim 1, further comprising at least a monomeric unit part of which will leave with an acid to allow the polymeric compound to be soluble in an alkali, in addition to the monomeric unit represented by Formula (I).

3. The polymeric compound according to claim 2, wherein the monomeric unit part of which will leave with an acid to allow the polymeric compound to be soluble in an alkali is a monomeric unit selected from monomeric units represented by following Formulae (IIa), (IIb), (IIc), and (IId):

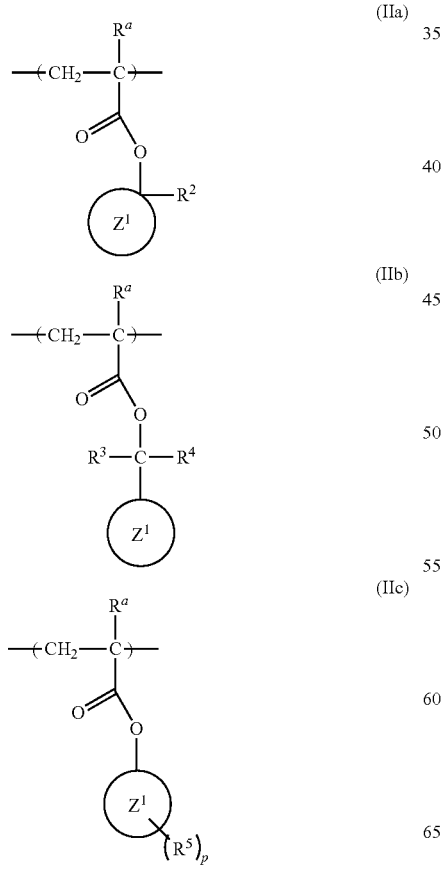

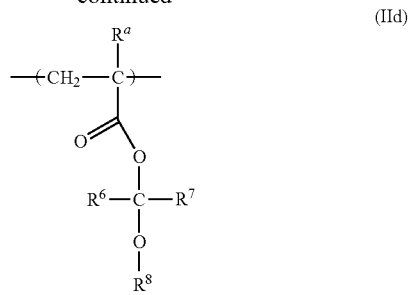

wherein

Ring $Z^1$ represents a substituted or unsubstituted alicyclic hydrocarbon ring having 5 to 20 carbon atoms;

$R^a$ represents a hydrogen atom, a halogen atom, or a substituted or unsubstituted alkyl group having 1 to 6 carbon atoms;

$R^2$, $R^3$, and $R^4$ are the same as or different from one another and each represent a substituted or unsubstituted alkyl group having 1 to 6 carbon atoms;

$R^5$s are substituents bound to Ring $Z^1$, are the same as or different from each other, and each represent oxo group, an alkyl group, a protected or unprotected hydroxyl group, a protected or unprotected hydroxyalkyl group, or a protected or unprotected carboxyl group, wherein at least one of $pR^5$s represents a —$COOR^c$ group, wherein $R^c$ represents a substituted or unsubstituted tertiary hydrocarbon group, a tetrahydrofuranyl group, a tetrahydropyranyl group, or an oxepanyl group;

"p" denotes an integer of 1 to 3;

$R^6$ and $R^7$ are the same as or different from each other and each represent a hydrogen atom or a substituted or unsubstituted alkyl group having 1 to 6 carbon atoms; and $R^8$ represents a hydrogen atom or an organic group, wherein at least two of $R^6$, $R^7$, and $R^8$ may be bound to each other to form a ring with an adjacent atom.

4. The polymeric compound according to any one of claims 1 to 3, further comprising at least a monomeric unit containing an alicyclic skeleton having at least one substituent, in addition to the monomeric unit represented by Formula (I).

5. The polymeric compound according to claim 4, wherein the monomeric unit containing an alicyclic skeleton having at least one substituent is a monomeric unit selected from monomeric units represented by following Formula (III):

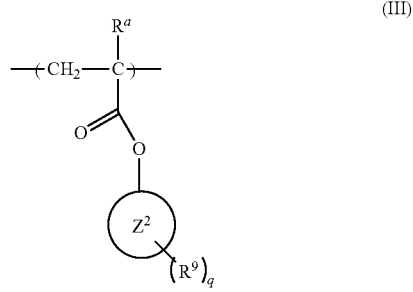

wherein

Ring $Z^2$ represents an alicyclic hydrocarbon ring having 6 to 20 carbon atoms;

$R^a$ represents a hydrogen atom, a halogen atom, or a substituted or unsubstituted alkyl group having 1 to 6 carbon atoms;

R⁹s are substituents bound to Ring $Z^2$, are the same as or different from each other, and each represent an oxo group, an alkyl group, a haloalkyl group, a halogen atom, a protected or unprotected hydroxyl group, a protected or unprotected hydroxyalkyl group, a protected or unprotected mercapto group, a protected or unprotected carboxyl group, a protected or unprotected amino group, or a protected or unprotected sulfonic group; and "q" is the number of R⁹s and denotes an integer of 1 to 5.

6. The polymeric compound according to claim 2, comprising at least the monomeric unit represented by Formula (I); the monomeric unit part of which will leave with an acid to allow the polymeric compound to be soluble in an alkali; and a monomeric unit containing an alicyclic skeleton having at least one substituent selected from hydroxyl group and hydroxymethyl group.

7. The polymeric compound according to claim 1, further comprising at least another monomeric unit having a lactone skeleton than the monomeric unit represented by Formula (I), in addition to the monomeric unit represented by Formula (I).

8. A photoresist composition comprising at least the polymeric compound according to claim 1; and a light-activatable acid generator.

9. A process for manufacturing a semiconductor device, the process comprising:
applying the photoresist composition according to claim 8 to a substrate to form a film;
drying the film;
directing light onto the film through a mask to form a latent image pattern; and
developing the latent image pattern.

10. A monomer having an electron-withdrawing substituent and a lactone skeleton, which is represented by following Formula (1):

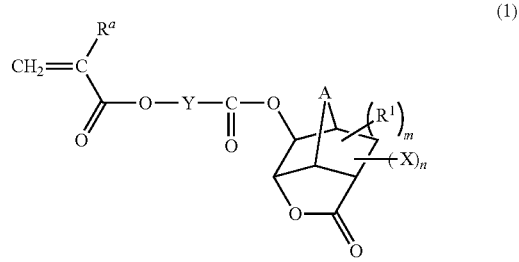

(1)

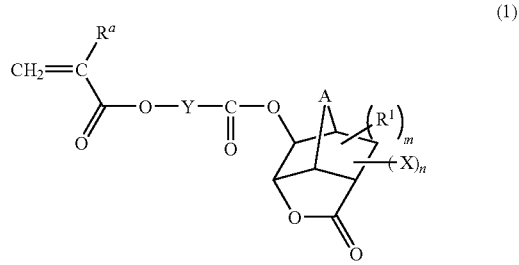

(1)

wherein
$R^a$ represents a hydrogen atom, a halogen atom, or a substituted or unsubstituted alkyl group having 1 to 6 carbon atoms;
$R^I$ is a substituent bound to the ring and represents a halogen atom, an alkyl or haloalkyl group having 1 to 6 carbon atoms, a hydroxyalkyl or hydroxyhaloalkyl group having 1 to 6 carbon atoms whose hydroxyl moiety may be protected by a protecting group, a carboxyl group which may form a salt, or a substituted oxycarbonyl group;
"A" represents an alkylene group having 1 to 6 carbon atoms, an oxygen atom, a sulfur atom, or nonbonding;
"m" is the number of $R^1$s and denotes an integer of 0 to 8;
Xs each independently represent an electron-withdrawing substituent selected from the group consisting of: fluorine-containing group, acyloxy group, cyano group, nitro group, sulfo group, alkanesulfonyl group, alkanesulfinyl group and alkoxysulfonyl group, and wherein at least one X is bound directly to the alpha position of the carbonyl group of the lactone ring;
"n" is the number of Xs bound to the ring and denotes an integer of 1 to 9; and
Y represents a methylene or a group composed of an alkylene group having 1 to 3 carbon atoms and an alkylene group having 1 or 2 carbon atoms bound with each other through an ester bond, wherein the $CH_2=C(R^a)COO$—Y—COO— group may have either endo or exo configuration.

11. A halogen-containing lactone compound represented by following Formula (6):

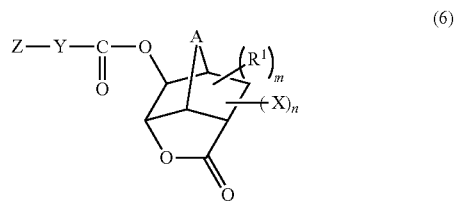

(6)

wherein
R¹s are substituents bound to the ring and each represent a halogen atom, an alkyl or haloalkyl group having 1 to 6 carbon atoms, a hydroxyalkyl or hydroxyhaloalkyl group having 1 to 6 carbon atoms whose hydroxyl moiety may be protected by a protecting group, a carboxyl group which may form a salt, or a substituted oxycarbonyl group;
"A" represents an alkylene group having 1 to 6 carbon atoms, an oxygen atom, a sulfur atom, or nonbonding;
"m" is the number of R¹s and denotes an integer of 0 to 8;
Xs each independently represent an electron-withdrawing substituent selected from the group consisting of: fluorine-containing group, acyloxy group, cyano group, nitro group, sulfo group, alkanesulfonyl group, alkanesulfinyl group and alkoxysulfonyl group, and wherein at least one X is bound directly to the alpha position of the carbonyl group of the lactone ring;
"n" is the number of Xs bound to the ring and denotes an integer of 1 to 9;
Z represents a chlorine atom, a bromine atom, or an iodine atom; and
Y represents a methylene or a group composed of an alkylene group having 1 to 3 carbon atoms and an alkylene group having 1 or 2 carbon atoms bound with each other through an ester bond, wherein the Z—Y—COO— group may have either endo or exo configuration.

12. A process for producing a monomer having an electron-withdrawing substituent and a lactone skeleton, the process comprising the step of reacting a halogen-containing lactone compound represented by following Formula (6):

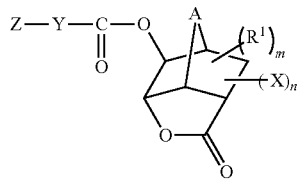
(6)

wherein
$R^1$s are substituents bound to the ring and each represent a halogen atom, an alkyl or haloalkyl group having 1 to 6 carbon atoms, a hydroxyalkyl or hydroxyhaloalkyl group having 1 to 6 carbon atoms whose hydroxyl moiety may be protected by a protecting group, a carboxyl group which may form a salt, or a substituted oxycarbonyl group;
"A" represents an alkylene group having 1 to 6 carbon atoms, an oxygen atom, a sulfur atom, or nonbonding;
"m" is the number of $R^1$s and denotes an integer of 0 to 8;
Xs each independently represent an electron-withdrawing substituent selected from the group consisting of: fluorine-containing group, acyloxy group, cyano group, nitro group, sulfo group, alkanesulfonyl group, alkanesulfinyl group and alkoxysulfonyl group, and wherein at least one X is bound directly to the alpha position of the carbonyl group of the lactone ring;
"n" is the number of Xs bound to the ring and denotes an integer of 1 to 9;
Z represents a chlorine atom, a bromine atom, or an iodine atom; and
Y represents a methylene or a group composed of an alkylene group having 1 to 3 carbon atoms and an alkylene group having 1 or 2 carbon atoms bound with each other through an ester bond, wherein the Z—Y—COO— group may have either endo or exo configuration
with an unsaturated carboxylic acid, or an alkali metal salt or alkaline earth metal salt thereof, represented by following Formula (7):

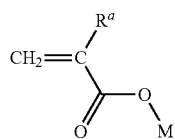
(7)

wherein
$R^a$ represents a hydrogen atom, a halogen atom, or a substituted or unsubstituted alkyl group having 1 to 6 carbon atoms; and
M represents a hydrogen atom, an alkali metal, or an alkaline earth metal, to give the monomer having an electron-withdrawing substituent and a lactone skeleton, represented by following Formula (1):

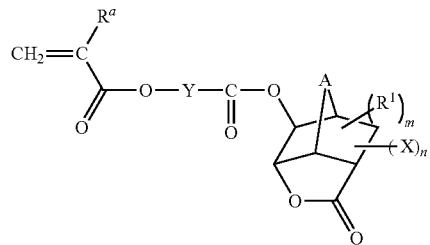
(1)

wherein
$R^a$ represents a hydrogen atom, a halogen atom, or a substituted or unsubstituted alkyl group having 1 to 6 carbon atoms;
$R^1$s are substituents bound to the ring and each represent a halogen atom, an alkyl or haloalkyl group having 1 to 6 carbon atoms, a hydroxyalkyl or hydroxyhaloalkyl group having 1 to 6 carbon atoms whose hydroxyl moiety may be protected by a protecting group, a carboxyl group which may form a salt, or a substituted oxycarbonyl group;
"A" represents an alkylene group having 1 to 6 carbon atoms, an oxygen atom, a sulfur atom, or nonbonding;
"m" is the number of $R^1$s and denotes an integer of 0 to 8;
Xs each independently represent an electron-withdrawing substituent selected from the group consisting of: fluorine-containing group, acyloxy group, cyano group, nitro group, sulfo group, alkanesulfonyl group, alkanesulfinyl group and alkoxysulfonyl group, and wherein at least one X is bound directly to the alpha position of the carbonyl group of the lactone ring;
"n" is the number of Xs bound to the ring and denotes an integer of 1 to 9; and
Y represents a methylene or a group composed of an alkylene group having 1 to 3 carbon atoms and an alkylene group having 1 or 2 carbon atoms bound with each other through an ester bond, wherein the $CH_2$=$C(R^a)COO$—Y—COO— group may have either endo or exo configuration.

* * * * *